United States Patent
van Hemert

(10) Patent No.: US 12,042,225 B2
(45) Date of Patent: Jul. 23, 2024

(54) DETECTION OF PATHOLOGIES IN OCULAR IMAGES

(71) Applicant: OPTOS PLC, Dunfermline (GB)

(72) Inventor: Jano van Hemert, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 132 days.

(21) Appl. No.: 17/942,132

(22) Filed: Sep. 10, 2022

(65) Prior Publication Data

US 2023/0000338 A1 Jan. 5, 2023

Related U.S. Application Data

(63) Continuation of application No. 16/721,902, filed on Dec. 19, 2019, now Pat. No. 11,503,994.

(30) Foreign Application Priority Data

Dec. 20, 2018 (EP) ..................................... 18214689

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *A61B 3/12* (2013.01); *A61B 3/14* (2013.01);
(Continued)

(58) Field of Classification Search
CPC ......... A61B 3/102; A61B 3/0025; A61B 3/12; A61B 3/14; A61B 5/4842; A61B 5/7267;
(Continued)

(56) References Cited

U.S. PATENT DOCUMENTS 9,931,032 B2 4/2018 Davis
2010/0208204 A1 8/2010 Mamura et al.
(Continued)

FOREIGN PATENT DOCUMENTS

CN 107636693 A 1/2018
CN 106231990 B 7/2019
(Continued)

OTHER PUBLICATIONS

Office Action dated Mar. 23, 2021, issued in Japanese Patent Application No. 2019-230618, including original Japanese version and English translation thereof (copies available in file history of parent U.S. Appl. No. 16/721,902).
(Continued)

*Primary Examiner* — Mohammed A Hasan
(74) *Attorney, Agent, or Firm* — FAEGRE DRINKER BIDDLE & REATH

(57) ABSTRACT

A computer-implemented method of searching for a region indicative of a pathology in an image of a portion of an eye acquired by an ocular imaging system, the method comprising: receiving image data defining the image; searching for the region in the image by processing the received image data using a learning algorithm; and in case a region in the image that is indicative of the pathology is found: determining a location of the region in the image; generating an instruction for an eye measurement apparatus to perform a measurement on the portion of the eye to generate measurement data, using a reference point based on the determined location for setting a location of the measurement on the portion of the eye; and receiving the measurement data from the eye measurement apparatus.

15 Claims, 10 Drawing Sheets

(51) Int. Cl.
*A61B 3/12* (2006.01)
*A61B 3/14* (2006.01)
*G06V 10/70* (2022.01)
*G06V 10/82* (2022.01)
*G06V 40/18* (2022.01)

(52) U.S. Cl.
CPC .............. *G06V 10/70* (2022.01); *G06V 10/82* (2022.01); *G06V 40/18* (2022.01)

(58) Field of Classification Search
CPC ........ A61B 3/063; G06V 10/70; G06V 10/82; G06V 40/18; G06V 2201/03; G06F 18/00; G06T 2207/10101; G06T 2207/30041; G06T 7/0012; G06T 2207/20081; G06T 2207/20084; G06T 7/11; G06T 7/70
USPC ....................................................... 351/206
See application file for complete search history.

(56) References Cited

U.S. PATENT DOCUMENTS

| | | | |
|---|---|---|---|
| 2012/0184845 A1 | 7/2012 | Ishikawa | |
| 2013/0208955 A1* | 8/2013 | Zhao | G16Z 99/00 382/128 |
| 2013/0208966 A1 | 8/2013 | Zhao | |
| 2014/0085606 A1 | 3/2014 | Miyasa et al. | |
| 2014/0276025 A1* | 9/2014 | Durbin | A61B 3/0025 600/407 |
| 2015/0110348 A1 | 4/2015 | Solanki et al. | |
| 2016/0335478 A1* | 11/2016 | Bredno | A61B 34/74 |
| 2017/0000338 A1 | 1/2017 | Davis | |
| 2018/0070815 A1 | 3/2018 | Miyasa et al. | |
| 2018/0140257 A1 | 5/2018 | Govindjee et al. | |
| 2018/0144470 A1 | 5/2018 | Govindjee et al. | |

FOREIGN PATENT DOCUMENTS

| | | |
|---|---|---|
| JP | 2010-35607 A | 2/2010 |
| JP | 2013-31527 A | 2/2013 |
| JP | 2014-188254 A | 10/2014 |
| JP | 2016-509914 A | 4/2016 |
| JP | 6025311 B2 | 11/2016 |
| JP | 2018121886 A | 8/2018 |

OTHER PUBLICATIONS

Examination Report dated May 12, 2021 issued in relation to Australian application No. 2019280075 (copy available file history of parent U.S. Appl. No. 16/721,902).

Extended European Search Report dated Jun. 6, 2019 relating to EP 18 214 689.4 (copy available in file history of parent U.S. Appl. No. 16/721,902).

"ReLayNet: Retinal Layer and Fluid Segmentation of Macular Optical Coherence Tomography using Fully Convolutional Network" by Abhijit Guha Roy et al., Cornell University Library (Apr. 7, 2017), XP080761372 (copy available in file history of parent U.S. Appl. No. 16/721,902).

Jelinek H F et al., "Machine learning and pattern classification in identification of indigenous retinal pathology", Engineering in Medicine and Biology Society, EMBC, 2011 33rd International Conference of the IEEE EMBS, pp. 5951-5954 (2011) (copy available in file history of parent U.S. Appl. No. 16/721,902).

Ruba et al., "Identification and segmentation of exudates using SVM classifier", IEEE Sponsored 2nd International Conference on Innovations in Information Embedded and Communication Systems (ICIIECS '15) XP033192484, (6 sheets) (2015) (copy available in file history of parent U.S. Appl. No. 16/721,902).

Communication pursuant to Article 94(3) EPC issued in European Application No. 18 214 689.4-1207, (7 sheets), Oct. 14, 2020 (copy available in file history of parent U.S. Appl. No. 16/721,902).

Examination Report issued Jul. 28, 2021 in Indian patent application No. 201944052478 (6 sheets) (copy available file history of parent U.S. Appl. No. 16/721,902).

Notice of Reasons for Refusal of Sep. 8, 2022 issued in Japanese patent application No. 2021-195247 (2 Sheets) (Machine English translation attached: 3 sheets).

* cited by examiner

DETECTION OF PATHOLOGIES IN OCULAR IMAGES

CROSS REFERENCE TO RELATED APPLICATIONS

This application is a continuation of U.S. application Ser. No. 16/721,902, filed Dec. 19, 2019, which is incorporated by reference herein in its entirety as if set forth fully herein.

FIELD

Example aspects herein generally relate to the field of image processing and, more particularly, to the processing of an ocular image to facilitate identification of the presence and/or location of a pathology in an imaged portion of an eye.

BACKGROUND

An ocular image of a portion of a subject's eye acquired by an ocular imaging system may have one or more regions containing some indication of a pathology that would not be present in a comparable image of a healthy eye, and the presence of such region(s) may be indicative of a disease or an otherwise unhealthy state of the subject. By way of an example, a fluorescein angiogram of the subject's retina may contain one or more regions where blood vessel leakage appears to have occurred, which can be a sign of macular oedema. Ocular images require an experienced ophthalmologist to acquire and assess. However, existing techniques are time-consuming for the ophthalmologist and/or the patient, and the assessment performed may be prone to error.

SUMMARY

The present inventors have devised, in accordance with a first example aspect herein, a computer-implemented method of searching for a region indicative of a pathology in an image of a portion of an eye acquired by an ocular imaging system. The method comprises receiving image data defining the image, and searching for the region in the image by processing the received image data using a learning algorithm trained on image data defining images of the portion of healthy eyes, and image data defining images of the portion of unhealthy eyes each having at least one region that is indicative of the pathology. In case a region in the image that is indicative of the pathology is found in the searching, a location of the region in the image is determined, an instruction is generated for an eye measurement apparatus to perform a measurement on the portion of the eye to generate measurement data, using a reference point based on the determined location for setting a location of the measurement on the portion of the eye, and the measurement data is received from the eye measurement apparatus.

The present inventors have also devised, in accordance with a second example aspect herein, a computer-implemented method of searching for the presence of a pathology in an image of a portion of an eye acquired by an ocular imaging system. The method comprises receiving image data defining the image, and searching for the presence of at least one of a plurality of different types of pathology in the image by processing the received image data using a learning algorithm trained on image data defining images of healthy eyes, and images of unhealthy eyes each having a respective one of the different types of pathology. The method further comprises, in case at least one of the plurality of different types of pathology is found to be present in the image, processes of: selecting, for each of at least one type of pathology found to be present in the image, a respective one of a plurality of different types of measurement modality which is to be used to perform a measurement on the portion of the eye; generating, for each of the at least one type of pathology found to be present in the image, a respective instruction for an eye measurement apparatus of the respective selected measurement modality to perform the measurement on the portion of the eye; and receiving measurement data of the measurement performed by the eye measurement apparatus of each selected measurement modality.

The present inventors have further devised, in accordance with a third example aspect herein, a computer program which, when executed by a computer, causes the computer to perform the method according to the first or the second example aspects herein.

The present inventors have further devised, in accordance with a fourth example aspect herein, a non-transitory computer-readable storage medium storing the computer program according to the third example aspect herein.

The present inventors have further devised, in accordance with a fifth example aspect herein, a signal carrying the computer program according to the third example aspect herein.

The present inventors have further devised, in accordance with a sixth example aspect herein, an apparatus for searching for a region indicative of a pathology in an image of a portion of an eye acquired by an ocular imaging system. The apparatus comprises a receiver module configured to receive image data defining the image. The apparatus further comprises a search module configured to search for the region in the image by processing the received image data using a learning algorithm trained on image data defining images of the portion of healthy eyes, and image data defining images of the portion of unhealthy eyes each having at least one region that is indicative of the pathology. The apparatus further comprises an instruction generating module configured to perform, in response to a region in the image that is indicative of the pathology being found by the search module, processes of: determining a location of the region in the image; and generating an instruction for an eye measurement apparatus to perform a measurement on the portion of the eye to generate measurement data, using a reference point based on the determined location for setting a location of the measurement on the portion of the eye. The receiver module is further configured to receive the measurement data from the eye measurement apparatus.

The present inventors have further devised, in accordance with a seventh example aspect herein, an apparatus for searching for the presence of a pathology in an image of a portion of an eye acquired by an ocular imaging system. The apparatus comprises a receiver module configured to receive image data defining the image and a search module configured to search for the presence of at least one of a plurality of different types of pathology in the image by processing the received image data using a learning algorithm trained on image data defining images of healthy eyes, and images of unhealthy eyes each having a respective one of the different types of pathology. The apparatus further comprises an instruction generating module configured to perform, in response to at least one of the plurality of different types of pathology being found to be present in the image by the search module, processes of: selecting, for each of at least one type of pathology found to be present in the image, a respective one of a plurality of different types of measurement modality which is to be used to perform a measurement on the portion of the eye; and generating, for each of the at least one type of pathology found to be present in the image, a respective instruction for an eye measurement apparatus of the respective selected measurement modality to perform the measurement on the portion of the eye. The receiver module is further configured to receive measurement data of the measurement performed by the eye measurement apparatus of each selected measurement modality.

BRIEF DESCRIPTION OF THE DRAWINGS

Embodiments of the invention will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EMBODIMENTS

In certain example embodiments described herein, an ocular image is processed to automatically detect a pathology in the ocular image using the image processing techniques hereinafter described, and then a further measurement on the eye is automatically instructed in order to acquire supplementary data that can allow the presence of the pathology to be determined (and/or to allow the pathology to be characterised) with a higher degree of confidence. For example, the eye may be imaged using a different imaging modality (for example, optical coherence tomography, OCT), or its functional response to light stimulation measured. By way of further example, in the case of a fluorescein angiogram in which the image processing detects a possible indication that blood vessel leakage has occurred in a region of the retina, an OCT scan of the region may be instructed, and thickness or volume measurements may be obtained from the data of the OCT scan in order to confirm the presence of the macular oedema and, where present, optionally diagnose its severity. Embodiments can thus facilitate fast and reliable detection of pathologies for early detection of disease, their advantages being most pronounced where the ocular image is a wide-field or ultra-wide-field image covering a large part of the retina or other portion of the eye.

Embodiments of the present invention will now be described in detail with reference to the accompanying drawings.

Embodiment 1

Figure 1:
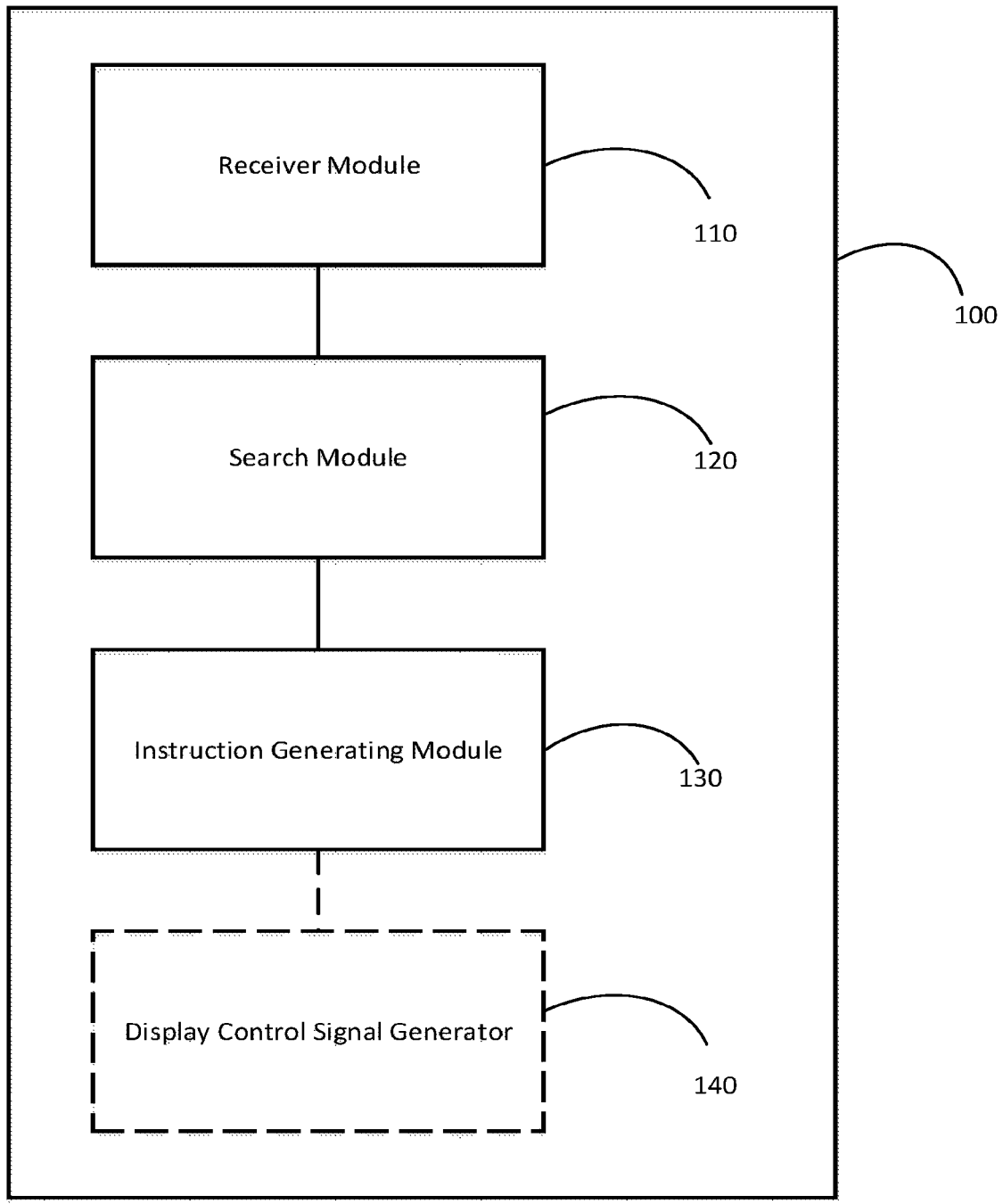
FIG. 1 is a schematic illustration of an apparatus for searching for a region indicative of a pathology in an ocular image, in accordance with a first example embodiment herein.
Figure 5:
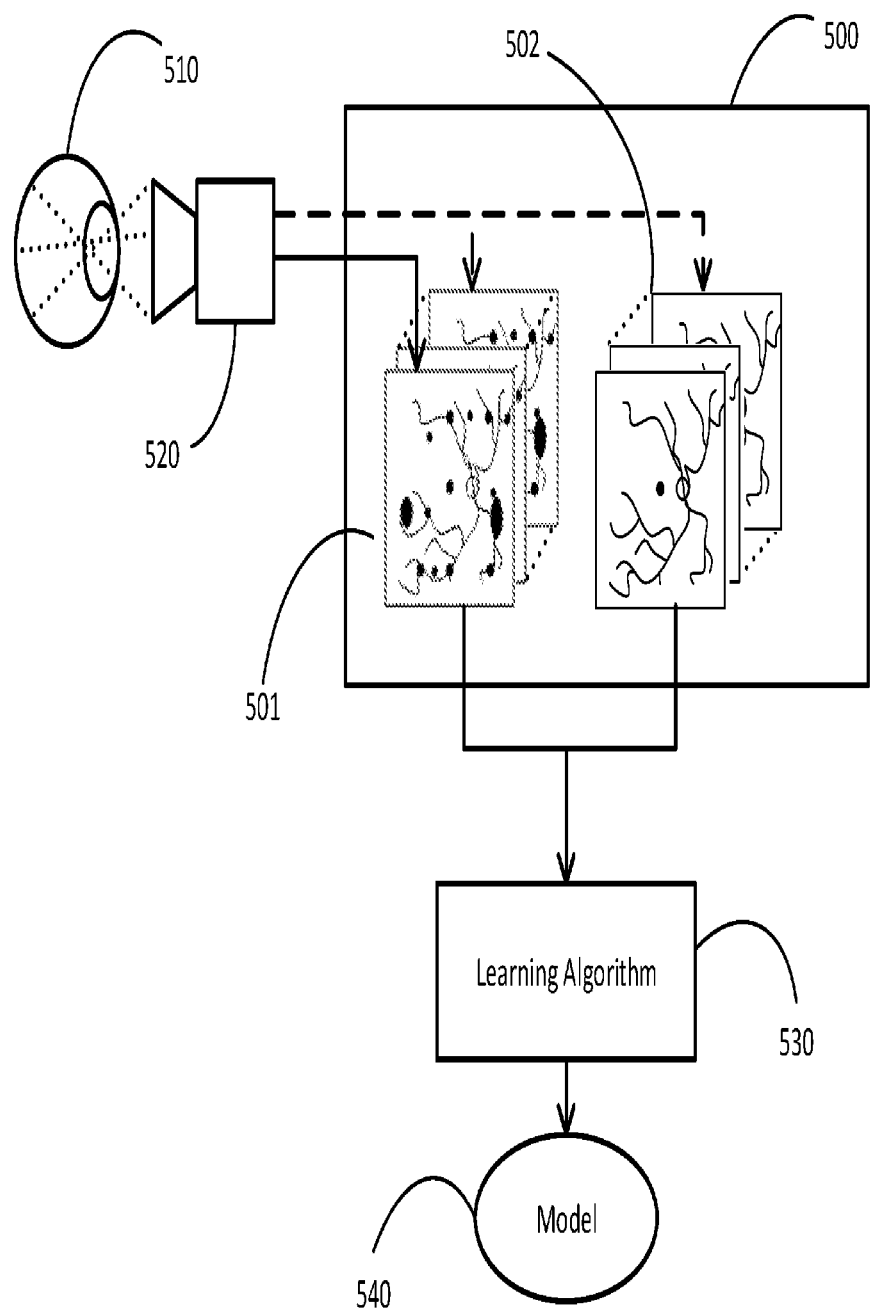
FIG. 5 is a schematic illustrating how a learning algorithm may be trained on image data defining images of the portion of healthy eyes, and image data defining images of the portion of unhealthy eyes each having at least one region that is indicative of a pathology, in accordance with a first example aspect herein.

FIG. 1 is a schematic illustration of an apparatus 100 according to a first example embodiment, for searching for a region indicative of a pathology in an image of a portion of an eye acquired by an ocular imaging system (shown at 520 in the schematic illustration of FIG. 5). The apparatus 100 comprises a receiver module 110 configured to receive image data defining an image produced by a ocular imaging system 520, and a search module 120 configured to automatically search for at least one region indicative of a pathology in the image, by processing the received image data using a learning algorithm which is described in detail below. The apparatus 100 further comprises an instruction generating module 130 configured to automatically perform, in response to a region in the image that is indicative of the pathology being found by the search module 120, processes of: determining a location of the region in the image and generating an instruction for an eye measurement apparatus to perform a measurement on the portion of the eye to generate measurement data, using a reference point based on the determined location for setting a location of the measurement on the portion of the eye. In cases where two or more such regions are found by the search module 120, these processes may be performed for each of the regions. The receiver module 110 is further configured to receive the measurement data from the eye measurement apparatus. Optionally, the apparatus 100 may, as in the present illustrated embodiment, comprise a display control signal generator 140 (this optional component being shown by the dashed lines in FIG. 1).

A region indicative of a pathology may be a region of the image defined by the received image data which contains image features indicative of a lesion, structural damage or any other abnormality that would not be present in a similarly-acquired image of a healthy eye.

The apparatus 100 may be configured to search for a region indicative of any pathology that may occur in the eye, which may include (but is not limited to), for example, glaucoma, moderate diabetic retinopathy, severe diabetic retinopathy, tumour, drusen, oedema and atrophy.

In the present example embodiment, the receiver module 110 is configured to receive image data defining an image of a portion of a retina of the eye, which has been generated by the ocular imaging system 520. However, in other example embodiments, the received image data may define an image of a portion of the eye other than the retina, for example a portion of the anterior segment of the eye, or a portion of the posterior segment of the eye. Furthermore, the received image data may, as in the present example embodiment, define a two-dimensional image, or it may alternatively define a three-dimensional image of the imaged portion of the eye. The received image data may be provided in any suitable format (whether compressed or uncompressed) known to those skilled in the art. The image data received by the receiver module 110 is of a first imaging modality (discussed in more detail below), and represents a result of imaging the retina of the eye using appropriately selected values for imaging parameters, which may include imaging resolution, aperture size, and wavelength.

The ocular imaging system 520 may be any ocular imaging system that is suitable for imaging the retina (or other selected portion) of the eye. The ocular imaging system 520 may, for example, be a fundus camera, or a type of scanning imaging system. By way of example, the ocular imaging system 520 of the present example embodiment is a scanning imaging system in the exemplary form of a scanning laser ophthalmoscope (SLO), which is configured to acquire images of the retina of a subject's eye. The SLO of the present example embodiment is configured to capture autofluorescence (AF) images (it may be configured to capture Red-Green (RG) reflectance images or images from other fluorescence modes), although it may alternatively or additionally be configured to acquire one or more other types of images. The SLO may, for example, be an ultra-wide field SLO (UWF-SLO) capable of generating an ultra-wide field image of up to 80% of a retinal surface. Alternatively, the ocular imaging system 520 may be of another imaging modality, for example an optical coherence tomography (OCT) scanner, in which case the image processing techniques described herein are applicable to the tomographic images acquired by the OCT scanner. As a further alternative, the ocular imaging system 520 may be a combined SLO-OCT scanner, in which case the image processing techniques described herein are applicable to both the SLO retinal scans and the OCT scans acquired by the combined SLO-OCT scanner.

The receiver module 110 is configured to receive image data defining the image acquired by the ocular imaging system 520 by any suitable means known to those versed in the art. For example, the receiver module 110 may receive the image data from the ocular imaging system 520 via a direct communication link (which may be provided by any suitable wired or wireless connection, e.g. a Universal Serial Bus (USB) or a Bluetooth™ connection), or an indirect communication link (which may be provided by a network comprising a Local Area Network (LAN), a Wide Area Network (WAN) and/or the Internet). Furthermore, the image data may be received by the receiver module 110 receiving (e.g. by reading from a storage medium such as a CD or hard disk, or receiving via a network such as the Internet) such image data after it has been acquired by the ocular imaging system.

Furthermore, the image data may be received by the receiver module 110 (and may furthermore subsequently be processed to search for a region indicative of a pathology in an image of a portion of an eye, as described below) as this image data is being generated by the ocular imaging system, i.e. the image data may be acquired "on the fly", without waiting for the ocular imaging system 520 to finish generating all of the image data that forms the image of the portion of the retina. However, in the present example embodiment, and for the purposes of this description, the receiver module 110 is configured to receive all of the image data defining the image of the portion of the eye before the search module 120 begins to process this image data.

In embodiments like the present illustrated embodiment, where the apparatus 100 comprises a display control signal generator 140, the display control signal generator 140 may be arranged to generate display control signals for controlling a display device (as shown at 215 in FIG. 2), such as an LCD screen or other type of visual display unit, to display both the location of the region indicative of the pathology in the image of the portion of the eye, and a representation of the received measurement data.

Figure 2:
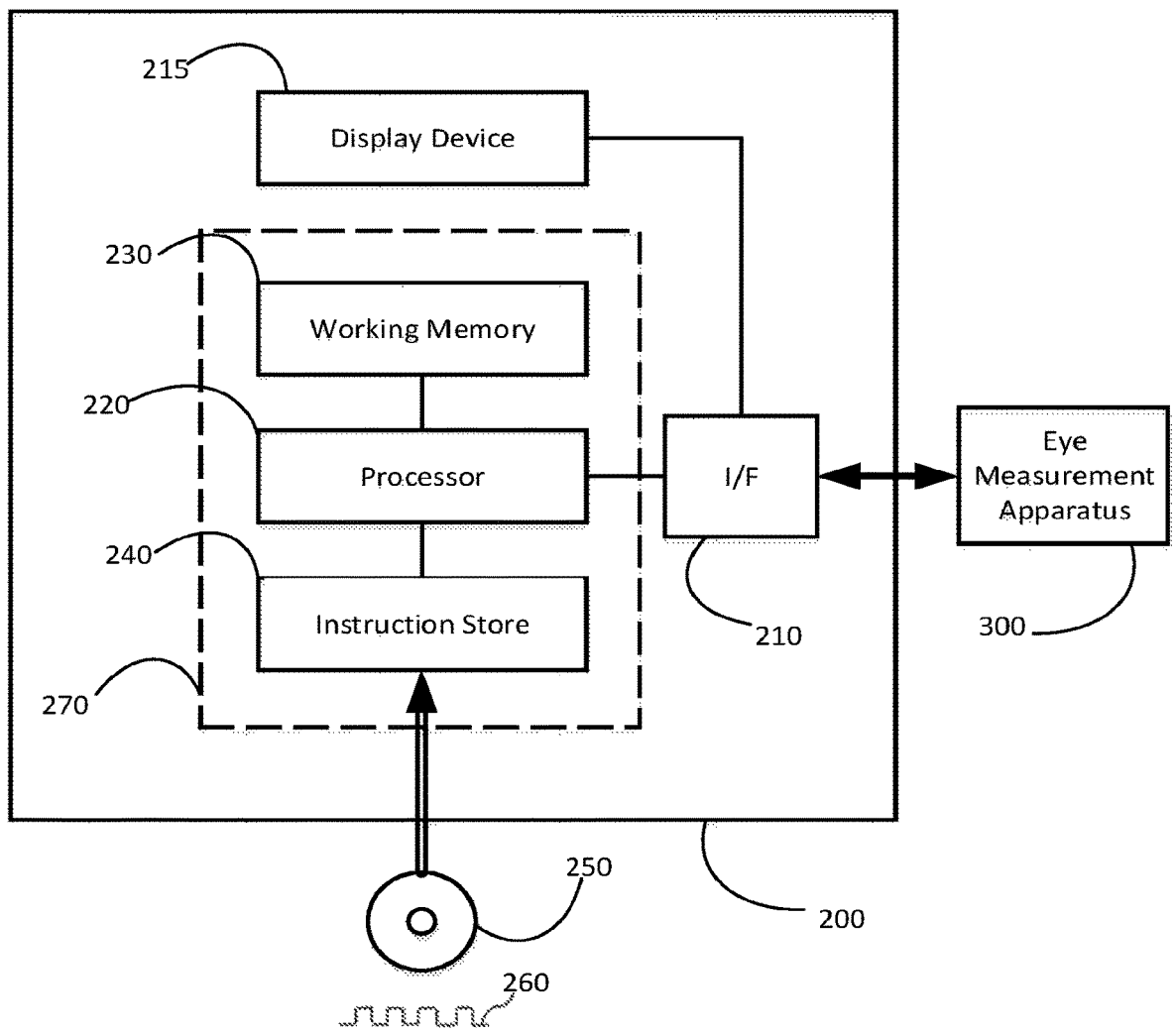
FIG. 2 is a block diagram illustrating an example signal processing hardware configuration of the apparatus of FIG. 1, according to an example embodiment herein.

FIG. 2 is a schematic illustration of a programmable signal processing hardware 200, which may, as in the present example embodiment, be configured to function as the apparatus 100 of FIG. 1. The programmable signal processing hardware 200 comprises a communication interface (I/F) 210 for receiving the image data described above, generating the instruction for the eye measurement apparatus 300 to perform the measurement on the portion of the eye to generate the measurement data, receiving the measurement data from the eye measurement apparatus 300, and, optionally, for outputting display control signals for controlling the display device 215 to display both the image of the portion of the eye and a representation of the measurement data. The signal processing apparatus 200 further comprises a processor (e.g. a Central Processing Unit, CPU, or Graphics Processing Unit, GPU) 220, a working memory 230 (e.g. a random access memory) and an instruction store 240 storing a computer program comprising the computer-readable instructions which, when executed by the processor 220, cause the processor 220 to perform various functions including those of the search module 120, instruction generating module 130 and, optionally, the display control signal generator 140 described above. The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions of the computer program can be input thereto from a computer program product, such as a non-transitory, computer-readable storage medium 250 in the form of a CD-ROM, DVD-ROM, etc. or a computer-readable signal 260 carrying the computer-readable instructions. In any case, the computer program, when executed by the processor, causes the processor to execute at least one of the methods of searching for a region indicative of a pathology, or the presence of a pathology, in an image of a portion of an eye acquired by an ocular imaging system described herein. It should be noted, however, that the apparatus 100 may alternatively be implemented in non-programmable hardware, such as an application-specific integrated circuit (ASIC).

In the present example embodiment, a combination 270 of the hardware components shown in FIG. 2, comprising the processor 220, the working memory 230 and the instruction store 240, is configured to perform functions of the search module 120 and instruction generating module 130, which functions will now be described in detail below. In embodiments like the present illustrated embodiment, where the apparatus 100 comprises a display control signal generator 140, the functionality of this optional component also be provided by the combination 270 of the hardware components, together with the communication I/F 210.

As will become more apparent from the following description of the operations performed by the apparatus 100 of the present example embodiment, the apparatus 100 automatically processes image data defining an image of the portion of an eye acquired by an ocular imaging system 520 to find, and record the location in the image of, each region that is indicative of pathology, and generates a corresponding instruction for an eye measurement apparatus 300 to perform a measurement on the portion of the eye to generate measurement data, using a reference point based on the recorded location of the respective region for setting a respective location of the measurement on the portion of the eye. The apparatus 100 thus acquires both the location of each image region suspected to contain a pathology, and additional measurement data related to the respective region. These different but complementary kinds of information that are automatically acquired by the apparatus 100 can be presented together to the medical practitioner for inspection, and may thus allow any pathology-containing regions of the received ocular image to be identified more quickly and with a greater degree of confidence than by inspecting the ocular image alone. For example, in example embodiments where the recorded location of the region in the image and the representation of the received measurement data are both displayed on the display device 215 (preferably overlaid on one another), a viewer of the display device 215 may be able to easily recognize whether, and where, such region is to be found in the image. It may not be as easy to do so from viewing either the recorded location of the region in the image, or the representation of the received measurement data, when either type of information is displayed alone on the display device 215. Similar advantages may occur in alternative example embodiments, where the recorded location of the region in the image and the received measurement data are processed automatically to identify regions of interest.

Figure 3:
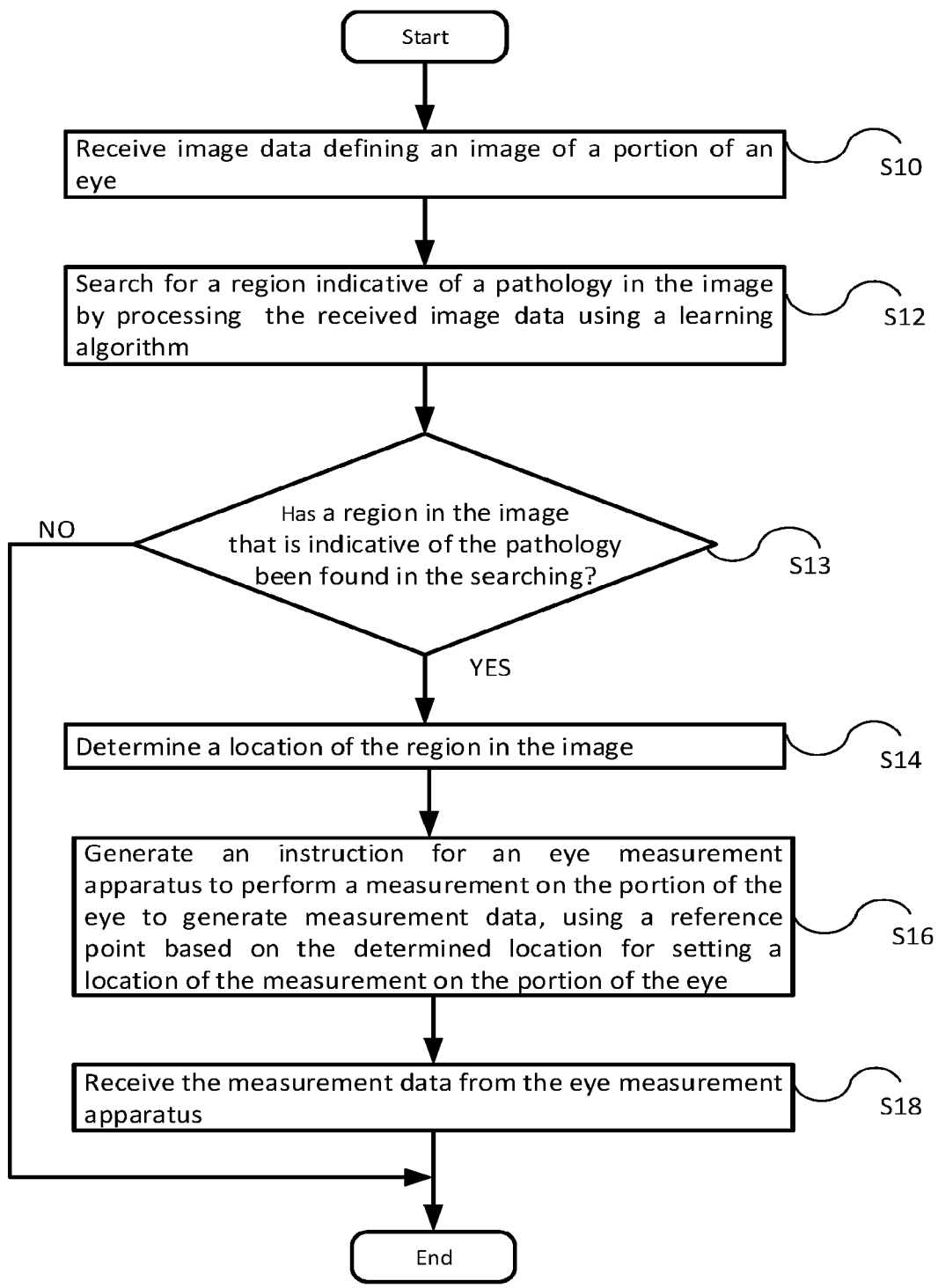
FIG. 3 is a flow diagram illustrating a process by which the apparatus of FIG. 1 searches for a region indicative of a pathology in an ocular image, in accordance with the first example embodiment herein.

FIG. 3 is a flow diagram illustrating a process by which the apparatus 100 of FIG. 1 searches for a region that is indicative of a pathology in an image of a portion of an eye acquired by an ocular imaging system 520, in accordance with the first example embodiment herein.

Figure 4A:
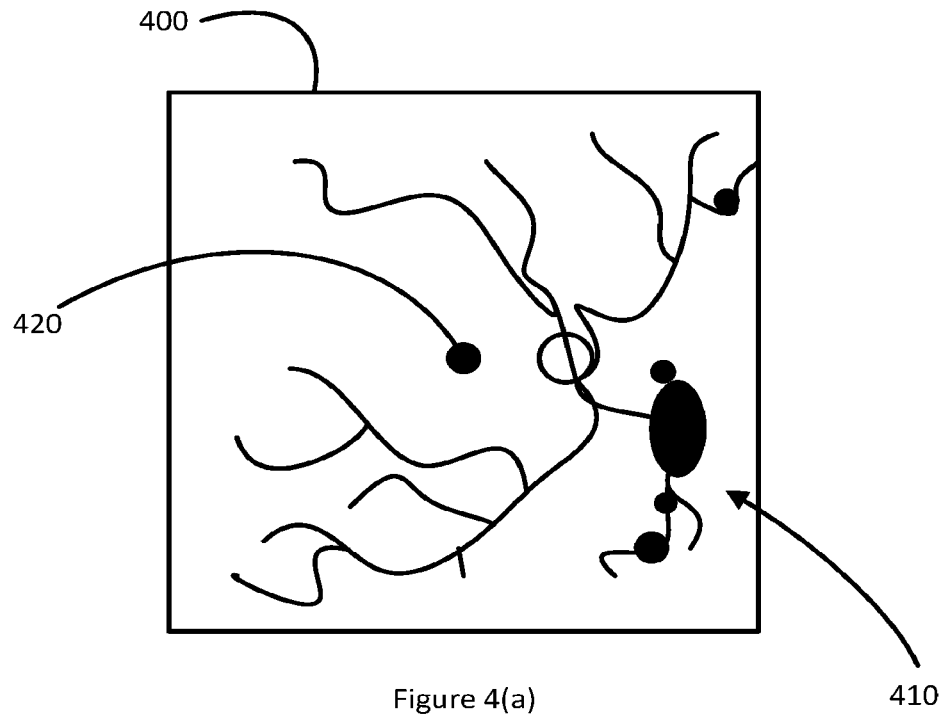
FIG. 4(a) is a schematic illustration of an image of a portion of the eye acquired by an ocular imaging system.

In process S10 of FIG. 3, the receiver module 110 receives image data of a first imaging modality, which has been acquired by the ocular imaging system 520. The imaging modality of the ocular imaging system may, for example, take one of the many different forms known to those versed in the art, including OCT, colour fundus photography, fluorescein angiography (FA), indocyanine green angiography (ICG) and autofluorescence (AF), among others. The received image data defines the image of a portion of the eye (in this example embodiment, the retina) acquired by the ocular imaging system 520. FIG. 4(a) is a schematic illustration of an image 400 of the portion of the retina defined by the received image data that has been acquired by an ocular imaging system 520.

In process S12 of FIG. 3, the search module 120 searches for the region (410 in FIG. 4(a)) indicative of a single type of pathology in the image 400 by processing the received image data using a learning algorithm which has been trained on image data defining images of the retina of healthy eyes, and image data defining images of the retina of unhealthy eyes each having at least one region that is indicative of the pathology. The location in the image 400 of each region 410 found in the search is recorded by the search module 120, for example in the working memory 230 in case the apparatus 100 is implemented in the programmable signal processing hardware 200 of FIG. 2.

FIG. 5 is a schematic representation illustrating how a learning algorithm may be trained on image data 502 defining images of healthy eyes, and image data 501 defining images of unhealthy eyes. The learning algorithm 530 is configured to learn from, and make predictions based on, input data by building a model 540 from an example training set 500 of input data, comprising the image data 502 defining images of the retina of healthy eyes, and the image data 501 defining images of the retina of unhealthy eyes. By way of example, image data 501 defines images of the portion of unhealthy eyes, each of which has a region indicative of severe diabetic retinopathy. The images defined by the image data 501 in the example training set 500 may be collected by acquiring images of the retinas of multiple subjects. More generally, each image is of the same portion of the eye (or of substantially the same portion of the eye 510 or of a part of the eye containing the same portion) as the image defined by the received image data. Furthermore, each image defined by the image data in the example training set 500 is acquired by the ocular imaging system 520 or by the same type of ocular imaging system and operating in the same imaging modality. By way of example, image data 501 defines images of the portion of unhealthy eyes, each of which has a region indicative of severe diabetic retinopathy.

In embodiments where the learning algorithm 530 is a supervised learning algorithm (such as a neural network, a support vector machine or an evolutionary algorithm, for example), each example image in the example training set 500 is a pair consisting of input image data defining an image of the portion of the eye and a desired output value indicating whether the image is of a portion of a "healthy" or "unhealthy" eye. The supervised learning algorithm 530 analyses the image data in the example training set 500 and produces a model 540, which can be used to classify new unseen image data defining an image of the portion of the eye as "healthy" or "unhealthy". As the learning algorithm 530 is trained on image data 501 defining images of unhealthy eyes having a single type of pathology only, the model 540 cannot distinguish between pathologies. It can only determine whether a region indicative of the pathology, for example, severe diabetic retinopathy, is present or not.

In process S12 of FIG. 3, the search module 120 may, in a modification of the present example embodiment, search for the region 410 in the image by searching for a region 410 in the image that is indicative not of a single type of pathology, but of one of a plurality of different types of pathology, by processing the received image data using the learning algorithm. Therefore, in the modification of the present example embodiment, the learning algorithm may be trained on image data defining images of the portion of unhealthy eyes each having a respective one of the different types of pathology.

Figure 6:
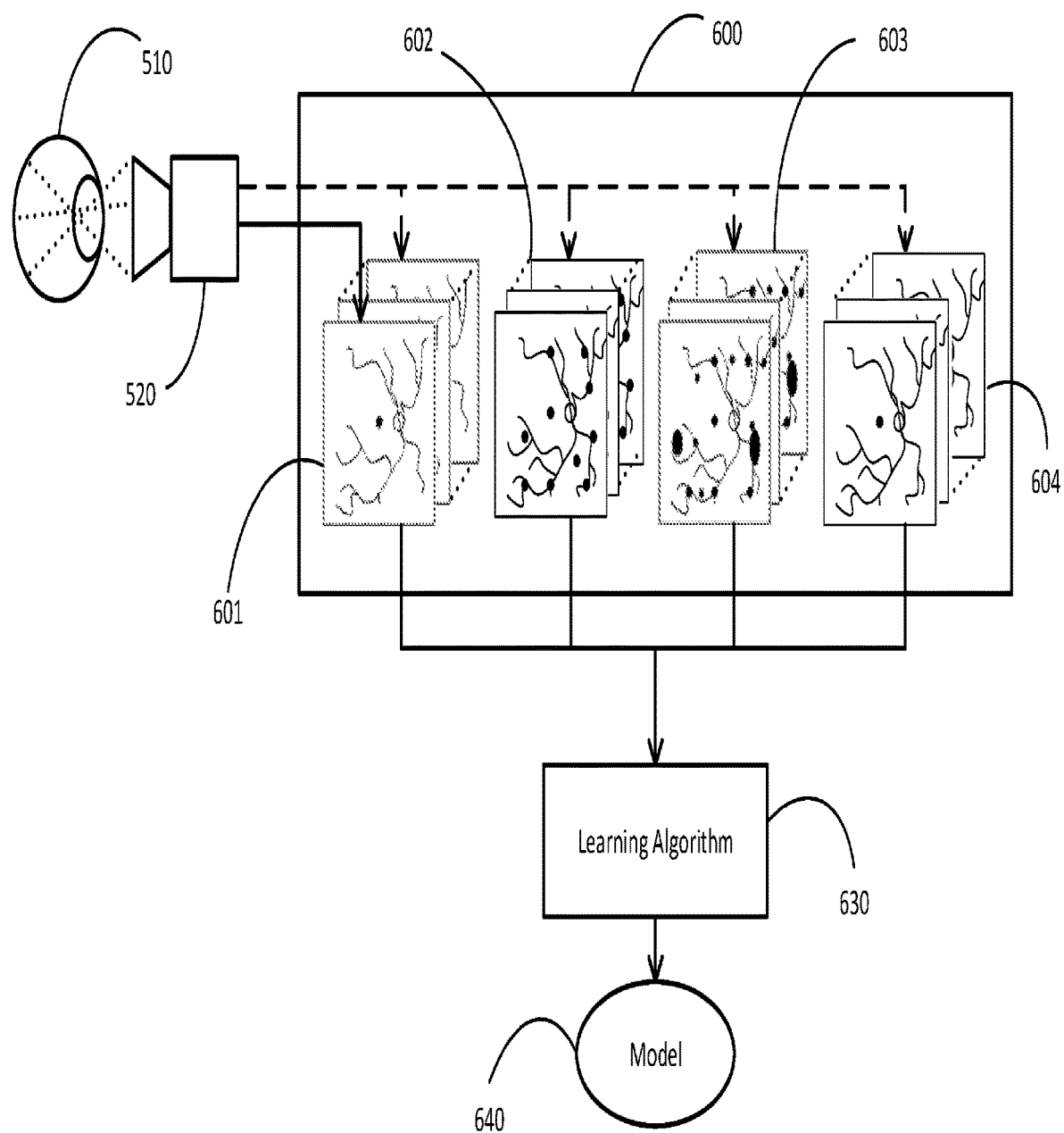
FIG. 6 is a schematic illustrating how a learning algorithm may be trained on image data defining images of a portion of healthy eyes, and image data defining images of the portion of unhealthy eyes each having at least one region that is indicative of a respective one of a plurality of different types of pathology, in accordance with a second example aspect herein.

FIG. 6 is a schematic illustrating how the modified learning algorithm 630 may be trained on image data 604 defining images of the retina of healthy eyes, and image data 601, 602, 603 defining images of the retina of unhealthy eyes, each having at least one region that is indicative of a respective one of a plurality of different types of pathology. By way of example, image data 601 defines images of the portion of unhealthy eyes which have glaucoma, image data 602 defines images of the portion of unhealthy eyes which have moderate diabetic retinopathy, and image data 603 defines images of the portion of unhealthy eyes which have severe diabetic retinopathy.

The learning algorithm 630 is configured to learn from, and make predictions based on, input data by building a model 640 from an example training set 600 of input data, comprising the image data 604 defining images of the retina of healthy eyes, and the image data 601, 602, 603 defining images of the retina of unhealthy eyes. The images defined by the image data 601 to 604 in the example training set 600 may be collected by acquiring images of the retinas of multiple subjects. More generally, each image is of the same portion of the eye (or of substantially the same portion of the eye 510 or of a part of the eye containing the same portion) as the image defined by the received image data. Furthermore, each image defined by the image data 610 to 604 in the example training set 600 is acquired by the ocular imaging system 520 or by the same type of ocular imaging system and operating in the same imaging modality.

The learning algorithm 630 may be a supervised learning algorithm. Thus, each example image of the portion of the eye 510 in the example training set 600 is associated with an indicator indicating whether that image is of a portion of a "healthy" or an "unhealthy" eye and, in cases where the image is of a portion of an "unhealthy" eye, also a second indicator indicating which one of the plurality of pathologies is present in the image. The supervised learning algorithm analyses the image data in the example training set 600 and produces a model 640, which can be used to classify new (previously unseen) image data defining an image of the portion of the eye as one of, for example: "healthy"; "unhealthy—glaucoma"; "unhealthy—moderate diabetic retinopathy"; and "unhealthy—severe diabetic retinopathy".

In will be evident to one skilled in the art that the apparatus 100 may be adapted to classify additional pathologies by expanding the training set 600 to include, for each of the additional pathologies, image data defining images of the retina (or other portion) of unhealthy eyes having that pathology, and associated indicators as described above. For example, the training set 600 may be expanded to include image data defining images of the portion of unhealthy eyes having a tumour and/or image data defining images of the portion of unhealthy eyes having oedema. Furthermore, any of the image data 601, 602, 603 defining images of the portion of unhealthy eyes may be removed or replaced with image data defining images of the portion of unhealthy eyes having a different pathology. A revised version of the model 640 may then be produced based on the modified training set 600.

The supervised learning algorithm 630 may, as in the present example embodiment, be a neural network. Neural networks automatically generate identifying characteristics by processing the input data, such as the image data in the example training set 600, without any prior knowledge.

The neural network may, as in the present example embodiment, be a convolutional neural network. Convolutional neural networks are particularly suitable to image and video recognition tasks.

Figure 7:
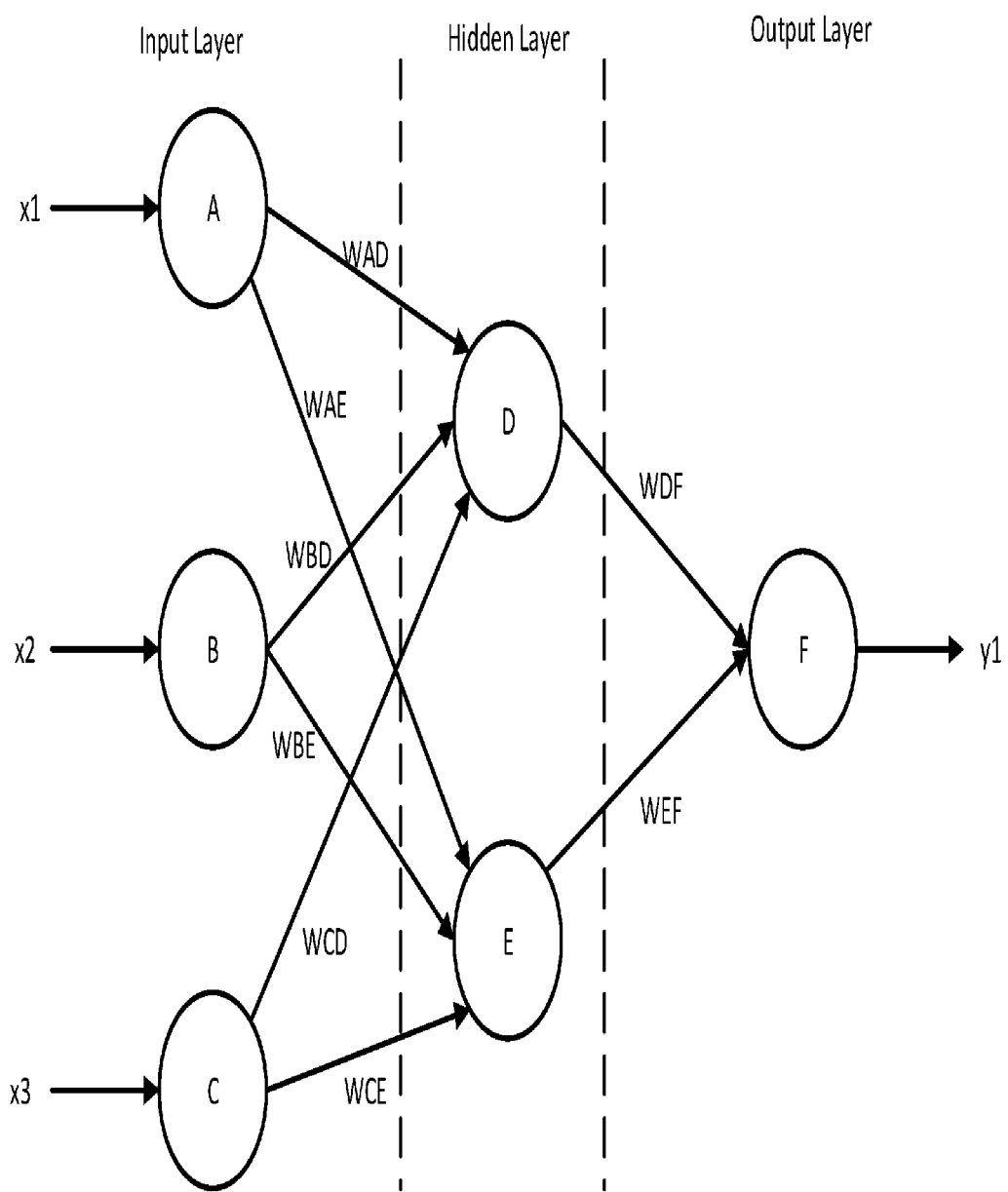
FIG. 7 is a schematic illustration of a convolutional neural network comprising artificial neurons in an input layer, a hidden layer, and an output layer.

As illustrated in FIG. 7, in general, a convolution neural network consists of an input layer and an output layer, as well as multiple hidden layers. Each of the layers is composed of a plurality of artificial neurons (labelled A to F in FIG. 7), and each layer may perform different kinds of transformations on their inputs. Each artificial neuron may be connected to multiple artificial neurons in adjacent layers. The output of each artificial neuron is computed by some non-linear function of the sum of its inputs. Artificial neurons and the connections therebetween typically have respective weights (WAD, WAE, etc. in FIG. 7) which determined the strength of the signal at a given connection. These weights are adjusted as learning proceeds, thereby adjusting the output of the convolutional neural network. Signals travel from the first layer (the input layer), to the last layer (the output layer), and may traverse the layers multiple times.

The output of the neural network may be viewed as a probability of the input image data containing identifying characteristics of the pathology and the classification may, as in the present example embodiment, comprise determining whether the output of the trained model 640 exceeds a predetermined threshold. The predetermined threshold may represent an acceptably low probability that the input image data contains identifying characteristics of a pathology and, therefore, a high probability that the eye of the subject is healthy.

In the case where the learning algorithm is a neural network, as in the present example embodiment, the search module 120 may be configured, as part of process S12 of FIG. 3, to search for the region 410 indicative of the pathology for in the image by deconstructing the neural network.

When image data defining an image 410 of the portion of the eye is input to the trained model 640, the trained model 640 classifies this image as "healthy", or as "unhealthy" and having a particular pathology (that is, the model 640 determines whether the input image data contains identifying characteristics of a pathology or not). Conventional convolutional neural networks do not output an explanation of this classification. Accordingly, the convolutional neural network can be deconstructed, that is, processed in order to determine which input variables of the input image data (that is, pixels of the image 400) were relevant to the output of the neural network. The input variables most relevant to the classification as "unhealthy" and having a certain pathology of the image 400 defined by the received image data correspond to the region 410 (or regions) that are indicative of the pathology.

In case the trained model 640 classified the image 400 defined by the received image data as "healthy" (that is, not containing any regions indicative of a pathology), the search module 120 may, as in the present example embodiment, be configured not to deconstruct the neural network.

Figure 8:
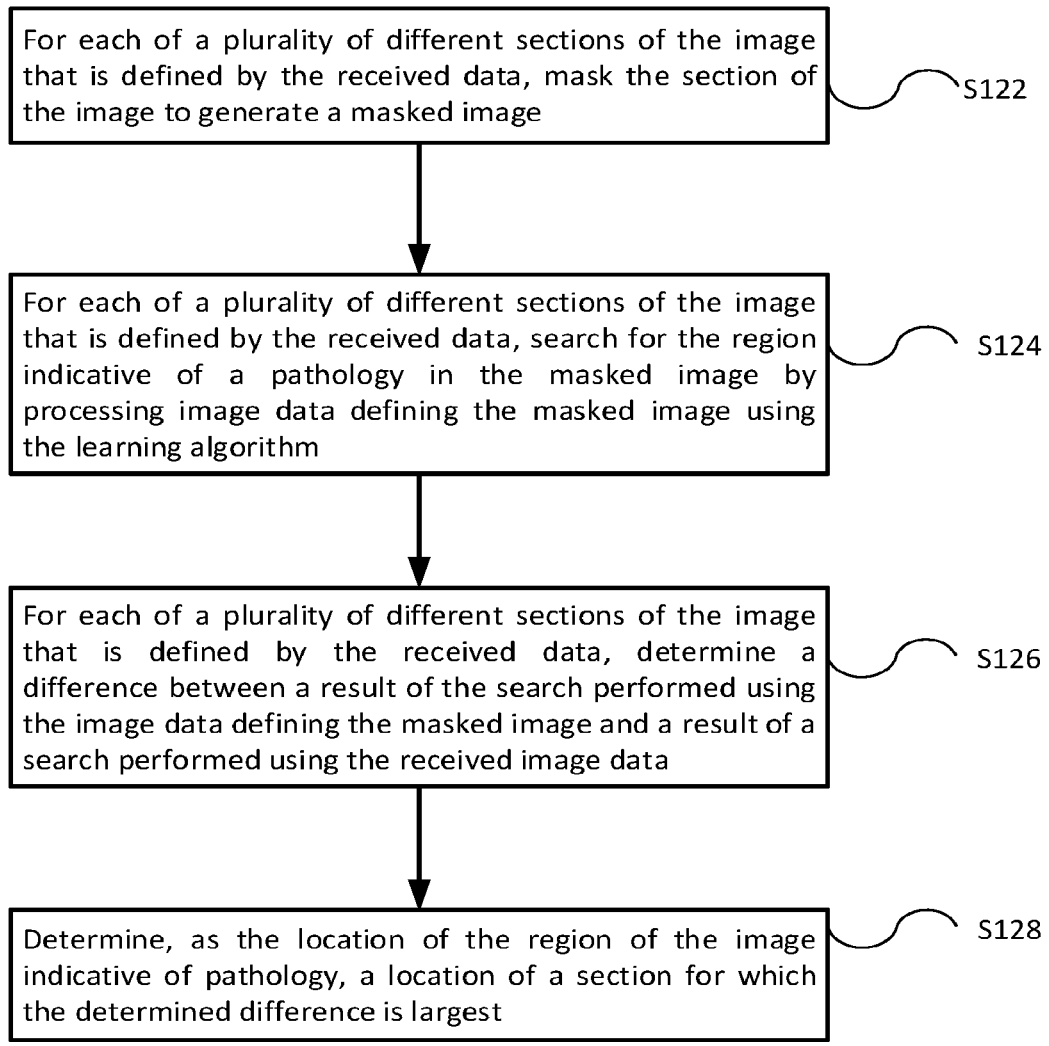
FIG. 8 is a flow diagram illustrating a process by which a search module of the apparatus of FIG. 1 may search for a region indicative of pathology in the image, according to an example embodiment herein.

In embodiments like the present illustrated embodiment, where the neural network is a convolutional neural network, the search module 120 may, as in the present example embodiment, be configured to deconstruct the convolutional neural network by performing the processes illustrated in the flow diagram of FIG. 8.

In S122 of FIG. 8, the search module 120 performs, for each of a plurality of different sections of the image 400, a process of masking the section of the image to generate a masked image.

In S124 of FIG. 8, the search module 120 performs, for each of a plurality of different sections of the image 400, a process of searching for the region in the masked image by processing image data defining the masked image using the learning algorithm.

In S126 of FIG. 8, the search module 120 performs, for each of a plurality of different sections of the image 400, a process of determining a difference between a first result which is a result of the search performed using the image data defining the masked image, and a second result which is a result of a search performed using the received image data (that is, the image data as received, in which the section of the image is not masked).

In S128 of FIG. 8, the search module 120 determines, as the location of the region 410 in the image 400, a location of a section for which the determined difference is largest.

Alternatively, where the neural network is a convolutional neural network, the search module 120 may be configured to deconstruct the convolutional neural network by:
  (i) determining a relevance of each input variable of the neural network to an output of the neural network by applying a Taylor decomposition to each layer of the neural network, from a top layer of the neural network to an input layer of the neural network; and
  (ii) determining the location to be recorded based on at least one section of the received image data corresponding to the most relevant input variables of the neural network.

Taylor decomposition is a method of explaining individual neural network predictions by decomposing the output of the neural network on its input variables. This method views the image 400 as a set of pixel values $x=\{x_p\}$, where p denotes a particular pixel. A function $f(x)$ quantifies the presence of a certain type of object, here a region 410 indicative of a pathology, in the image 400. A function value $f(x)=0$ indicates an absence of it. On the other hand, a function value $f(x)>0$ expresses its presence with a certain degree of certainty, or in a certain amount. The Taylor decomposition method assigns each pixel p in the image a relevance score $R_p(x)$, that indicates for an image x to what extent the pixel p contributes to explaining the classification decision $f(x)$. The relevance of each pixel can be stored in a heat map denoted by $R(x)=\{R_p(x)\}$ of same dimensions as x and can be visualized as an image. Accordingly, the location of the region can be determined as the location of the most relevant pixels in the heat map.

As a further alternative, where the neural network is a convolutional neural network, the search module 120 may be configured to deconstruct the convolutional neural network by determining a deconvolution of the convolutional neural network. In particular, the convolution neural network may be deconstructed by training a multi-layer deconvolution network which takes, as an input, the output of the convolutional neural network and provides, as an output, a probability map of the same size as the image input to the convolutional neural network which indicates the probability of each pixel belonging to one of the predefined classes. Accordingly, the location of the region may be determined as the location of the pixels having the highest probability of belonging to one of the predetermined classes (that is, the highest probability of having one of the plurality of different types of pathology).

Therefore, the search module 120 may, as in the present example embodiment, be configured to search for the region 410 indicative of a pathology in the image by identifying, as the region 410 indicative of a pathology, the pixels of the image 400 defined by the received image data that are most relevant to the output of the neural network.

Referring again to FIG. 3, in process S13, the search module 120 determines whether a region in the image that is indicative of the pathology has been found as a result of the search performed in process S12. If a region in the image that is indicative of the pathology has been found as a result of the search performed in process S12, the process proceeds to S14, otherwise the process ends.

In process S14 of FIG. 3, the instruction generating module 130 determines the location in the image of the region 410 which has been found by the search module 120. The location may, for example, be recorded by the search module 120 in the working memory 230 of the hardware configuration 200 illustrated in FIG. 2, and read from the working memory by the instruction generating module 130 in S14.

Figure 4B:
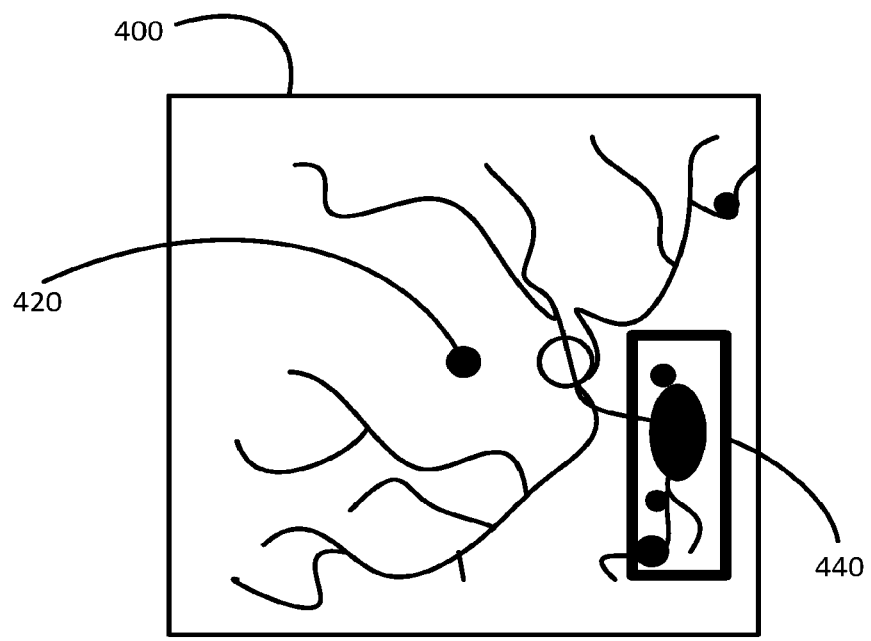
FIG. 4(b) is an annotated version of the image shown in FIG. 4(a), showing a region which is indicative of a pathology that has been found, in accordance with an example aspect herein.

In embodiments like the present example embodiment, where process results of the apparatus 100 are displayed on a display device 215 as herein described, the determined location may, as illustrated in FIG. 4(a), serve to center or otherwise position an overlay graphical element, such as the boundary box 440 illustrated in FIG. 4(b), over the region 410 of the image 400 found to contain the pathology.

In process S16 of FIG. 3, the instruction generating module 130 generates an instruction for an eye measurement apparatus 300 to perform a measurement on the portion of the eye to generate measurement data, using a reference point based on the determined location for setting a location of the measurement on the portion of the eye. The instruction generated in process S16 of FIG. 3 may be provided to the eye measurement apparatus 300 by any suitable means known to those versed in the art.

In embodiments like the present illustrated embodiment, the determined location is a location in the image 400 of a group of one or more pixels constituting the region 410. In order to determine a reference point that can be used to set a location of the measurement to be performed by the eye measurement apparatus 300 on the portion of the eye, the location recorded by the search module 120 in S12 can be transformed into a corresponding set of one or more control parameters for steering the eye measurement apparatus 300 to perform its measurement at substantially the same location in/on the eye as that imaged by the ocular imaging system 520. This can be done in one of a number of different ways.

For example, the instruction generating module 130 may use a mapping between pixel coordinate values from images acquired by the SLO and corresponding values of the control parameters, which may be provided in the form of a look-up table or a function defined by a set of parameters, for example. The mapping may be determined by calibration, using techniques known to those skilled in the art.

In process S18 of FIG. 3, the receiver module 110 receives the measurement data from the eye measurement apparatus 300, and the process then ends.

The eye measurement apparatus 300 may be of any kind of apparatus that allows a supplementary measurement of the subject's eye to be made, which could be used to verify that the region found by the search module 120 does (or is highly likely to) contain an imaged pathology. The eye measurement apparatus 300 may, for example, measure a functional response of the subject's eye to stimulation by light in response to an instruction generated by the instruction generating module 130, and communicate data representing the measured functional response to the receiver module 110.

Alternatively, the eye measurement apparatus 300 may, as in the present embodiment, be configured to perform, as the measurement on the retina (or other selected portion of the eye, as noted above), an image capture process of a second imaging modality to image a region of the retina, using the aforementioned reference point for setting, as the location of the measurement, a location of the region of the retina to be imaged in the image capture process, wherein the second imaging modality is different to the first imaging modality (i.e. SLO in the present example embodiment). Thus, in the present example embodiment, where a region in the image that is indicative of the pathology is found in S12 of FIG. 2, the instruction generating module 120 generates in S16 of FIG. 3, as the instruction for the eye measurement apparatus 300 to perform the measurement on the portion of the eye, an instruction for the eye measurement apparatus 300 to perform the image capture process using the reference point for setting, as the location of the measurement, a location of a region in the portion of the eye to be imaged in the image capture process. The receiver module 110 then receives in process S18 of FIG. 3, as the measurement data, image data of the second imaging modality acquired by the eye measurement apparatus 300. It is noted that a single, multimodal ocular imaging system capable of acquiring ocular images of two or more different imaging modalities (e.g. a combined SLO-OCT imaging system) may provide the functionality of the ocular imaging system 520 and the eye measurement apparatus 300. The ocular imaging system 520 and the eye measurement apparatus may alternatively be provided as separate components.

The mapping discussed above may rely on the subject's eye being positioned and oriented in relation to the eye measuring apparatus in a predetermined way. While this may be a good assumption in any practical applications, it may not hold true in all cases. Where this assumption does not hold, it may be preferable to define the location of the region found by the search module 120 in relation to an anatomical feature (e.g. the fovea) that is recognisable in both the image acquired by the ocular imaging system 520 and the image of a different modality that is acquired by the eye measurement apparatus 300 of the present example embodiment. The location of the region relative to the position of the fovea in the image 400 may then be transformed into a corresponding location relative to the position of the fovea in an image acquired by the eye measurement apparatus 300.

The reference point may be used to set the location of the measurement on the portion of the eye in any suitable way. For example, the eye measurement apparatus 300 may be controlled to image (or more generally perform any other kind of measurement on) a region of a predetermined size that is centred on a location on the subject's retina corresponding to the reference point.

In the modification of the first example embodiment described above, where the search module 120 searches for a region 410 in the image that is indicative of one of a plurality of different types of pathology by processing the received image data using the learning algorithm, the instruction generating module 130 performs, in response to a region 410 in the image 400 that is indicative of one of the plurality of different types of pathology being found by the search module 120, a process of selecting, for the one of the plurality of different types of pathology and as the second imaging modality, a respective one of a plurality of different types of imaging modality which is to be used to perform the image capture process on the retina of the eye. In the modification of the first embodiment, the instruction generating module 130 may, for example, select the respective one of a plurality of different types of imaging modality, which is to be used to perform the image capture process on the subject's retina, by consulting a look-up table (LUT) in which an indicator of each of the plurality of different types of pathology is stored in association with a respective indicator of one of the plurality of different types of imaging modality, and using the one of the plurality of different types of pathology found by the search module 120 as a search key.

For example, in a case where the one of the plurality of different types of pathology is glaucoma, the instruction generating module 130 may generate an instruction for the eye measurement apparatus 300 to perform, as the image capture process of the second imaging modality, an OCT scan of the region on the retina of the subject's eye. The receiver module 110 may then receive in S18 of FIG. 3, as the measurement data, image data of the OCT scan, which the apparatus 100 can process to obtain complementary data that is useful for detecting the glaucoma (and optionally estimating its severity), namely a measurement of a retinal nerve fibre layer and/or an optic nerve head of the eye.

As a further example, in a case where the one of the plurality of different types of pathology is severe diabetic retinopathy, the instruction generating module 130 may generate an instruction for the eye measurement apparatus 300 to perform, as the image capture process of the second imaging modality, an OCT scan of a region of a retina of the eye. The receiver module 110 may then receive in S18 of FIG. 3, as the measurement data, image data of the OCT scan, which the apparatus 100 can process to obtain complementary data that is useful for detecting the severe diabetic retinopathy (and optionally estimating its severity), namely measurements of macular thickness.

As another example, in a case where the one of the plurality of different types of pathology is a tumour, the instruction generating module 130 may generate an instruction for the eye measurement apparatus 300 to perform, as the image capture process of the second imaging modality, a high-density OCT B-scan of the region in the retina of the eye. The receiver module 110 may then receive in S18 of FIG. 3, as the measurement data, image data of the high-density OCT B-scan, which can be useful for detecting the tumour (and optionally estimating its size).

As a yet further example, in a case where the one of the plurality of different types of pathology is drusen, the instruction generating module 130 may generate an instruction for the eye measurement apparatus 300 to perform, as the image capture process of the second imaging modality, an OCT B-scan of the region in the retina of the eye. The receiver module 110 may then receive in S18 of FIG. 3, as the measurement data, image data of the OCT B-scan, which can be useful for detecting the presence of drusen or estimating their size and/or number. This data can be valuable in diagnosing age-related macular degeneration at an early stage, for example.

Furthermore, in a case where the one of the plurality of different types of pathology is oedema or atrophy, the instruction generating module 130 may generate an instruction for the eye measurement apparatus 300 to perform, as the image capture process of the second imaging modality, an OCT scan of the region in the retina of the eye. The receiver module 110 may then receive in S18 of FIG. 3, as the measurement data, image data of the OCT scan, which can be useful for detecting the oedema (or atrophy, as the case may be), and optionally estimating its severity.

In the modification of the first example embodiment described above, the search module 120 searches for a region 410 in the image that is indicative of one of a plurality of different types of pathology by processing the received image data using the learning algorithm, and the instruction generating module 130 performs, in response to a region 410 in the image 400 that is indicative of one of the plurality of different types of pathology being found by the search module 120, a process of selecting, for the one of the plurality of different types of pathology and as the second imaging modality, a respective one of a plurality of different types of imaging modality which is to be used to perform the image capture process on the retina of the eye. However, as noted above, the eye measurement apparatus 300 need not be configured to acquire an image of the retina (or, more generally, any other selected portion of the eye) but may instead perform a different kind of measurement on the eye. Moreover, the eye measurement apparatus 300 may be multi-modal in the sense of being operable in a selected one of a plurality of different measurement modalities. In such variants, the instruction generating module 130 may perform, in response to a region 410 in the image 400 that is indicative of one of the plurality of different types of pathology being found by the search module 120, processes of: selecting, for the one of the plurality of different types of pathology, a respective one of a plurality of different types of measurement modality for a measurement to be performed on the eye; and generating, as the instruction for the eye measurement apparatus 300 to perform the measurement on the portion of the eye, an instruction for an eye measurement apparatus 300 of the selected measurement modality to perform the measurement on the portion of the eye, using the reference point for setting the location of the measurement on the portion of the eye.

In a second modification of the first example embodiment, the eye measurement apparatus 300 may be an ocular imaging apparatus of the same imaging modality as the ocular imaging system 520 which, similar to the first embodiment, does not distinguish between different types of pathology. In this second modification, the receiver module 110 is configured to receive image data representing a result of imaging the portion of the eye using a first value of an imaging parameter, the imaging parameter being an imaging resolution, an aperture size or wavelength used in the imaging. The instruction generating module 130 is configured to perform, in response to a region 410 in the image 400 that is indicative of the pathology being found by the search module 120, a process of generating, as the instruction for the eye measurement apparatus 300 to perform the measurement on the portion of the eye, an instruction for the eye measurement apparatus 300 to perform an image capture process using a second value of the imaging parameter to image a region in the portion of the eye, again using the reference point for setting, as the location of the measurement, a location of a region in the portion of the eye to be imaged in the image capture process, wherein the second value of the imaging parameter is different from the first value of the imaging parameter. The receiver module 110 is configured to receive from the eye measurement apparatus 300, as the measurement data, the image data representing the result of imaging the region in the portion of the eye using the second value of the imaging parameter and the received image data and the received measurement data are of the same imaging modality.

For example, in the second modification, the ocular imaging system 520 may be configured to acquire image data defining the image by imaging the portion of the eye at a first imaging resolution, and the instruction generating module 130 may be configured to generate, in response to a region in the image that is indicative of pathology being found by the search module 120, an instruction for the eye measurement apparatus 300 to perform an image capture process at a second, higher imaging resolution to image the region in more detail.

Embodiment 2

Figure 9:
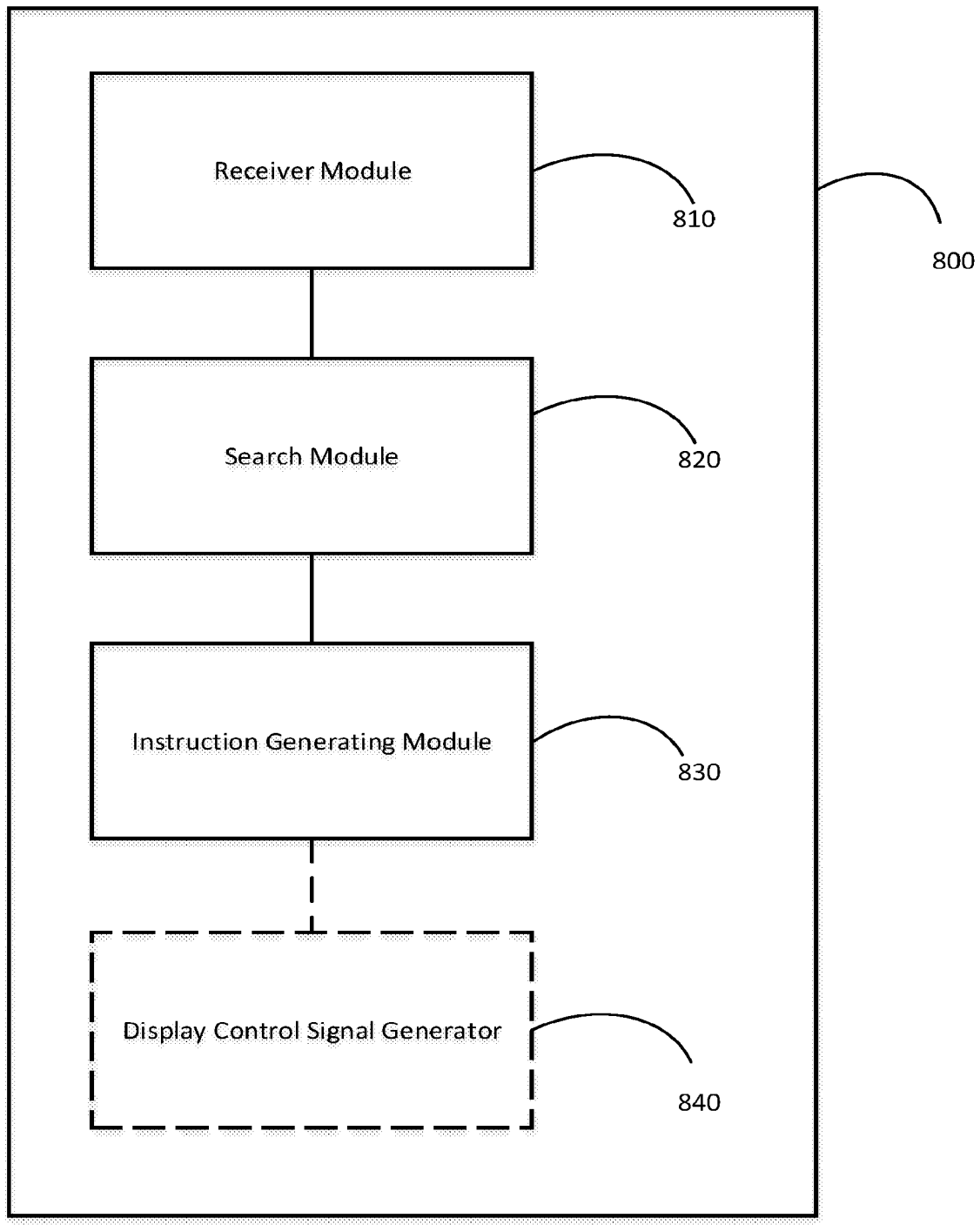
FIG. 9 is a schematic illustration of an apparatus for searching for the presence of a pathology in an ocular image, in accordance with an example embodiment herein.

FIG. 9 is a schematic illustration of an apparatus 800 for searching for the presence of a pathology in an image of a portion of an eye acquired by an ocular imaging system (520 in FIG. 5), in accordance with a second example embodiment herein. The apparatus 800 of the second example embodiment differs from the apparatus 100 of FIG. 1 in that the apparatus of FIG. 9 is not required to determine the location of a region indicative of a pathology in the received image 400.

The apparatus 800 comprises a receiver module 810 configured to receive image data defining an image produced by a ocular imaging system 520, and a search module 820 configured to search for the presence of at least one of a plurality of different types of pathology in the image. The apparatus 800 further comprises an instruction generating module 830 configured to perform, in response to at least one of the plurality of different types of pathology being found to be present in the image by the search module 820, processes of: selecting, for each of at least one type of pathology found to be present in the image, a respective one of a plurality of different types of measurement modality which is to be used to perform a measurement on the portion of the eye; and generating, for each of the at least one type of pathology found to be present in the image, a respective instruction for an eye measurement apparatus of the respective selected measurement modality to perform the measurement on the portion of the eye. The receiver module 810 is further configured to receive measurement data of the measurement performed by the eye measurement apparatus of each selected measurement modality. Optionally, the apparatus 800 may, as in the present illustrated embodiment comprise a display control signal generator 840 (this optional component being shown by the dashed lines in FIG. 9).

The apparatus 800 may be configured to search for the presence of any pathology, (including, for example, glaucoma, moderate diabetic retinopathy, severe diabetic retinopathy, tumour, drusen, oedema and atrophy), as discussed above in relation to the first embodiment.

In the present example embodiment, the receiver module 810 is configured to receive image data defining an image of a portion of a retina of the eye, which has been generated by the ocular imaging system 520. However, in other example embodiments, the received image data may define an image of a portion of the eye other than the retina, for example a portion of the anterior segment of the eye, or a portion of the posterior segment of the eye.

The ocular imaging system 520 may, as in the present example embodiment, be a scanning laser ophthalmoscope. Alternatively, the ocular imaging system may be any ocular imaging system described above in relation to the first embodiment.

The receiver module 810 may be configured to receive image data defining the image acquired by the ocular imaging system 520 by any of the means discussed above in relation to the first embodiment.

As will become more apparent from the following description of the operations performed by the apparatus 800 of the example embodiment, the apparatus 800 automatically processes image data defining an image of the portion of an eye acquired by an ocular imaging system 520 to search for the presence of at least one of a plurality of different types of pathology in the image and, when at least one of the plurality of different types of pathology is found to be present in the image, selects for each of at least one type of pathology found to be present in the image a respective one of a plurality of different types of measurement modality which is to be used to perform a measurement on the portion of the eye. A respective instruction for an eye measurement apparatus of the respective selected measurement modality to perform the measurement on the portion of the eye is then generated for each of the at least one type of pathology found to be present in the image. The apparatus 800 thus acquires both the image suspected to contain a particular type of pathology, and additional measurement data of a measurement modality that is related to the suspected type of pathology. These different but complementary kinds of information that are automatically acquired by the apparatus 800 may allow any pathology-containing ocular image to be identified quickly and with a high degree of confidence.

The apparatus 800 of FIG. 9 may be implemented by a signal processing hardware configuration, such as that shown in the FIG. 2, or by any other suitable means.

Figure 10:
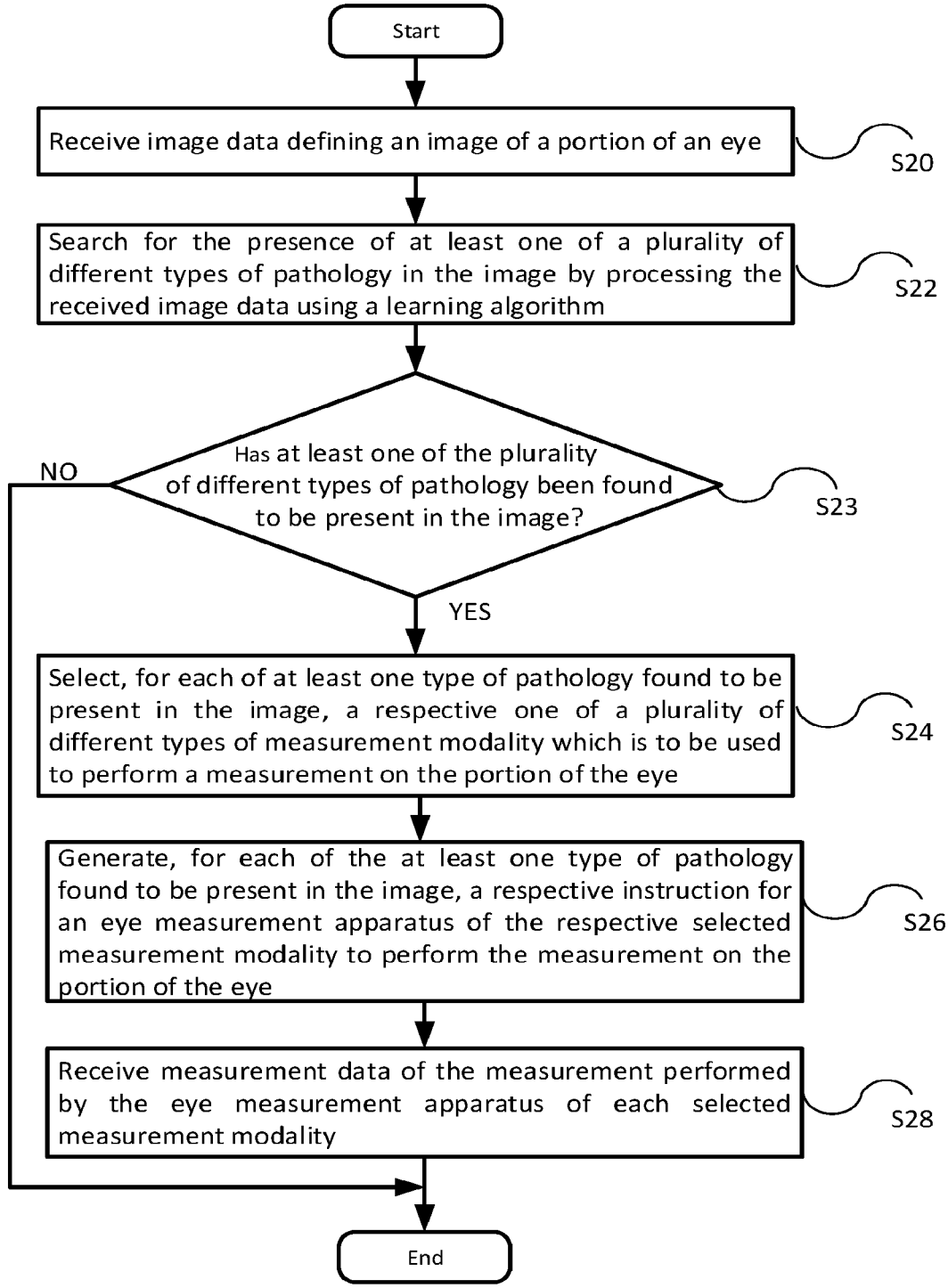
FIG. 10 is a flow diagram illustrating a process by which the apparatus of FIG. 9 searches for the presence of a pathology in an ocular image, in accordance with an example embodiment herein.

FIG. 10 is a flow diagram illustrating a process by which the apparatus 800 of FIG. 9 searches for the presence of a pathology in an image of a portion of an eye acquired by an ocular imaging system 520, in accordance with the second example embodiment herein.

In process S20 of FIG. 10, the receiver module 810 receives image data defining the image of the portion of the eye acquired by the SLO (as an example of the ocular imaging system 520).

In process S22 of FIG. 10, the search module 820 searches for the presence of at least one of a plurality of different types of pathology in the image by processing the received image data using a learning algorithm trained on image data defining images of healthy eyes, and images of unhealthy eyes each having a respective one of the different types of pathology. The learning algorithm may be trained as discussed above in relation to FIG. 6 in order to classify input image data defining an image of the portion of an eye as "healthy" or as "unhealthy" and having a particular pathology.

The apparatus 800 is not required to record a location of a region indicative of pathology in the image. Therefore, the apparatus 800 may, as in the present example embodiment, not process the learning algorithm in order to determine which input variables of the input image data (that is, pixels of the image defined by the received image data) were relevant to the output (that is, the finding that one of a plurality of different types of pathology is present). Alternatively, in other embodiments, such processing may optionally be carried out by the apparatus 800 as part of S22 of FIG. 10 in order to identify a reference point.

In process S23, the search module 820 determines whether at least one of the different types of pathology has been found to be present in the image, as a result of the search performed in process S22. If at least one of the different types of pathology has been found to be present in the image as a result of the search performed in process S22, the process proceeds to S24, otherwise the process ends.

In process S24 of FIG. 10, in response to at least one of the plurality of different types of pathology being found to be present in the image by the search module 820, the instruction generating module 830 performs the process of selecting, for each of at least one type of pathology found to be present in the image, a respective one of a plurality of different types of measurement modality which is to be used to perform a measurement on the portion of the eye.

The instruction generating module 830 may select a respective one of a plurality of different types of measurement modality by any of the means described above in relation to the apparatus 100 of FIG. 1.

In process S26 of FIG. 10, in response to at least one of the plurality of different types of pathology being found to be present in the image by the search module 820, the instruction generating module 830 performs the process of generating, for each of the at least one type of pathology found to be present in the image, a respective instruction for an eye measurement apparatus of the respective selected measurement modality to perform the measurement on the portion of the eye.

The instruction may be generated substantially as discussed above in relation to apparatus 100 of FIG. 1. However, in embodiments like the present illustrated embodiment where the apparatus 800 does not search for a region indicative of a pathology, the instruction generating module 830 need not use a reference point based on a recorded location of a region indicative of pathology for setting a location of the measurement on the portion of the eye. As part of process S26 of FIG. 10, the instruction generating module 130 may, as in the present example embodiment, generate, for each of the at least one type of pathology found to be present in the image, a respective instruction for an eye measurement apparatus of the respective selected measurement modality to perform the measurement on the same portion of the eye as imaged by the ocular imaging system.

In process S28 of FIG. 10 the receiver module 810 receives measurement data of the measurement performed by the eye measurement apparatus of each selected measurement modality. The receiver module 810 may receive measurement data by any of the means discussed above in relation of the first embodiment.

Some of the embodiments described above are summarised in the following examples E1 to E52:

E1. A computer-implemented method of searching for a region (410) indicative of a pathology in an image (400) of a portion of an eye acquired by an ocular imaging system (520), the method comprising:
  receiving (S10) image data defining the image (400);
  searching (S12) for the region (410) in the image (400) by processing the received image data using a learning algorithm (530; 630) trained on image data (502; 604) defining images of the portion of healthy eyes, and image data (601, 602, 603; 501) defining images of the portion of unhealthy eyes each having at least one region that is indicative of the pathology; and
  in case a region (410) in the image (400) that is indicative of the pathology is found in the searching:
    determining (S14) a location of the region (410) in the image (400);
    generating (S16) an instruction for an eye measurement apparatus (300) to perform a measurement on the portion of the eye to generate measurement data, using a reference point based on the determined location for setting a location of the measurement on the portion of the eye; and
  receiving (S18) the measurement data from the eye measurement apparatus (300).

E2. The computer-implemented method of E1, wherein searching (S12) for the region (410) in the image (400) comprises searching for a region (410) in the image (400) that is indicative of one of a plurality of different types of pathology by processing the received image data using the learning algorithm (630), the learning algorithm being trained on image data (601, 602, 603) defining images of the portion of unhealthy eyes each having a respective one of the different types of pathology, and
  in case a region (410) in the image (400) that is indicative of one of the plurality of different types of pathology is found in the searching (S12):

the method further comprises selecting, for the one of the plurality of different types of pathology, a respective one of a plurality of different types of measurement modality for a measurement to be performed on the eye; and the method comprises generating (S16), as the instruction for the eye measurement apparatus (300) to perform the measurement on the portion of the eye, an instruction for an eye measurement apparatus (300) of the selected measurement modality to perform the measurement on the portion of the eye, using the reference point for setting the location of the measurement on the portion of the eye.

E3. The computer-implemented method of E1, wherein
the received image data is image data of a first imaging modality,
the eye measurement apparatus (300) is configured to perform, as the measurement on the portion of the eye, an image capture process of a second imaging modality to image a region in the portion of the eye, and to acquire, as the measurement data, image data of the second imaging modality, the second imaging modality being different than the first imaging modality, and
in the case that a region (410) in the image (400) that is indicative of the pathology is found in the searching (S12), the method comprises:
generating (S16), as the instruction for the eye measurement apparatus (300) to perform the measurement on the portion of the eye, an instruction for the eye measurement apparatus (300) to perform the image capture process using the reference point for setting, as the location of the measurement, a location of a region in the portion of the eye to be imaged in the image capture process; and
receiving (S18) from the eye measurement apparatus (300), as the measurement data, image data of the second imaging modality defining an image of the region in the portion of the eye.

E4. The computer-implemented method of E3, wherein
searching (S12) for the region (410) in the image (400) comprises searching for a region (410) in the image (400) that is indicative of one of a plurality of different types of pathology by processing the received image data using the learning algorithm (630), the learning algorithm being trained on the image data (601, 602, 603) defining images of the portion of unhealthy eyes each having a respective one of the different types of pathology, and
in case a region (410) in the image (400) that is indicative of one of the plurality of different types of pathology is found in the searching (S12), the method further comprises selecting, for the one of the plurality of different types of pathology and as the second imaging modality, a respective one of a plurality of different types of imaging modality which is to be used to perform the image capture process on the portion of the eye.

E5. The computer-implemented method of E4, wherein:
in a case where the one of the plurality of different types of pathology is glaucoma, the method comprises generating (S16) an instruction for the eye measurement apparatus to perform, as the image capture process of the second imaging modality, an optical coherence tomography, OCT, scan of the region in the portion of the eye, and to acquire, as the measurement data, image data of the OCT scan;
in a case where the one of the plurality of different types of pathology is severe diabetic retinopathy, the method comprises generating (S16) an instruction for the eye measurement apparatus to perform, as the image capture process of the second imaging modality, an optical coherence tomography, OCT, scan of a region of a retina of the eye, and to acquire, as the measurement data, image data of the OCT scan;
in a case where the one of the plurality of different types of pathology is a tumour, the method comprises generating (S16) an instruction for the eye measurement apparatus to perform, as the image capture process of the second imaging modality, a high-density optical coherence tomography, OCT, B-scan of the region in the portion of the eye, and to acquire, as the measurement data, image data of the high-density OCT B-scan;
in a case where the one of the plurality of different types of pathology is drusen, the method comprises generating (S16) an instruction for the eye measurement apparatus to perform, as the image capture process of the second imaging modality, an optical coherence tomography, OCT, B-scan of the region in the portion of the eye, and to acquire, as the measurement data, image data of the OCT B-scan;
in a case where the one of the plurality of different types of pathology is oedema or atrophy, the method comprises generating (S16) an instruction for the eye measurement apparatus to perform, as the image capture process of the second imaging modality, an optical coherence tomography, OCT, scan of the region in the portion of the eye, and to acquire, as the measurement data, image data of the OCT scan.

E6. The computer-implemented method of E1, wherein, in case the region (410) in the image (400) that is indicative of the pathology is found in the searching, the method comprises generating (S16), as the instruction for the eye measurement apparatus to perform the measurement on the portion of the eye, an instruction for the eye measurement apparatus to measure a functional response of the eye to light stimulation, using the reference point for setting the location of the measurement which is based on the determined location.

E7. The computer-implemented method of E1, wherein
the received image data represents a result of imaging the portion of the eye using a first value of an imaging parameter, the imaging parameter being one of an imaging resolution, an aperture size and wavelength used in the imaging,
the eye measurement apparatus is configured to perform, as the measurement on the portion of the eye, an image capture process using a second value of the imaging parameter to image a region in the portion of the eye, and to acquire, as the measurement data, image data representing a result of imaging the region using the second value of the imaging parameter, wherein the second value of the imaging parameter is different from the first value of the imaging parameter, and the received image data and the acquired image data are of the same imaging modality, and
in the case that a region (410) in the image (400) that is indicative of the pathology is found in the searching, the method comprises:

generating (S16), as the instruction for the eye measurement apparatus to perform the measurement on the portion of the eye, an instruction for the eye measurement apparatus to perform the image capture process, using the reference point for setting, as the location of the measurement, a location of a region in the portion of the eye to be imaged in the image capture process; and receiving (S18) from the eye measurement apparatus, as the measurement data, the image data representing the result of imaging the region (410) in the portion of the eye using the second value of the imaging parameter.

E8. The computer-implemented method of any of E1 to E7, further comprising generating instructions for controlling a display unit (215) to display the location of the region (410) in the image (400) of the portion of the eye and a representation of the received measurement data.

E9. The computer-implemented method of any of E1 to E8, wherein the learning algorithm (530; 630) is a supervised learning algorithm.

E10. The computer-implemented method of E9, wherein the supervised learning algorithm comprises a neural network, and the region (410) indicative of the pathology is searched for in the image (400) by deconstructing the neural network.

E11. The computer-implemented method of E10, wherein the neural network is a convolutional neural network, and the neural network is deconstructed by:
performing, for each of a plurality of different sections of the image (400) that is defined by the received image data, processes of:
masking (S122) the section of the image (400) to generate a masked image;
searching (S124) for the region in the masked image by processing image data defining the masked image using the learning algorithm; and
determining (S126) a difference between a result of the search performed using the image data defining the masked image and a result of a search performed using the received image data; and
determining (S128), as the location of the region (410) in the image (400), a location of a section for which the determined difference is largest.

E12. The computer-implemented method of E10, wherein the neural network is a convolutional neural network, and the convolutional neural network is deconstructed by:
determining a relevance of each input variable of the neural network to an output of the neural network by applying a Taylor decomposition to each layer of the neural network, from a top layer of the neural network to an input layer of the neural network; and
determining the location of the region (410) in the image (400) based on at least one section of the received image data corresponding to the most relevant input variables of the neural network.

E13. The computer-implemented method of E10, wherein the neural network is a convolutional neural network, and the convolutional neural network is deconstructed by determining a deconvolution of the convolutional neural network.

E14. A computer-implemented method of searching for the presence of a pathology in an image (400) of a portion of an eye acquired by an ocular imaging system (520), the method comprising:

receiving (S20) image data defining the image (400);
searching (S22) for the presence of at least one of a plurality of different types of pathology in the image (400) by processing the received image data using a learning algorithm (630) trained on image data defining images (502) of healthy eyes, and images (601, 602, 603) of unhealthy eyes each having a respective one of the different types of pathology; and
in case at least one of the plurality of different types of pathology is found to be present in the image (400):
selecting (S24), for each of at least one type of pathology found to be present in the image (400), a respective one of a plurality of different types of measurement modality which is to be used to perform a measurement on the portion of the eye;
generating (S26), for each of the at least one type of pathology found to be present in the image (400), a respective instruction for an eye measurement apparatus (300) of the respective selected measurement modality to perform the measurement on the portion of the eye; and
receiving (S28) measurement data of the measurement performed by the eye measurement apparatus (300) of each selected measurement modality.

E15. The computer-implemented method of E14, further comprising, in case at least one of the plurality of different types of pathology is found to be present in the image (400):
for each of the at least one of the different types of pathology found to be present in the image, searching for a respective region (410) in the image (400) that is indicative of the respective type of pathology, by processing the received image data using the learning algorithm (630), and recording a location of the respective region (410) in the image (400), wherein
a respective instruction for the eye measurement apparatus (300) of each selected measurement modality to perform a measurement on the eye using a reference point for locating the measurement which is based on the respective recorded location is generated.

E16. The computer-implemented method of E15, wherein, in case at least one of the plurality of different types of pathology is found to be present in the image (400),
for each of the at least one of the different types of pathology found to be present in the image (400):
a respective one of a plurality of different types of imaging modality which is to be used to image the portion of the eye is selected as the respective one of the plurality of different types of measurement modality;
a respective instruction for an eye measurement apparatus (300) of the selected imaging modality to image the portion of the eye, using a reference point for locating a region of the eye to be imaged which is based on the respective recorded location, is generated as the respective instruction for the eye measurement apparatus (300) of the selected measurement modality; and
respective image data of the imaging performed by the eye measurement apparatus (300) of the selected imaging modality is received as the measurement data of the measurement performed by the eye measurement apparatus (300).

E17. The computer-implemented method of E16, wherein:
- in a case where one of the plurality of different types of pathology found to be present in the image (400) is glaucoma, the method comprises generating (S26), as the respective instruction for the eye measurement apparatus (300) of the selected imaging modality to image the portion of the eye, an instruction for the eye measurement apparatus (300) to perform an optical coherence tomography, OCT, scan of the region in the portion of the eye, and to acquire, as the measurement data, image data of the OCT scan;
- in a case where one of the plurality of different types of pathology found to be present in the image (400) is severe diabetic retinopathy, the method comprises generating (S26), as the respective instruction for the eye measurement apparatus (300) of the selected imaging modality to image the portion of the eye, an instruction for the eye measurement apparatus (300) to perform an optical coherence tomography, OCT, scan of a region of a retina of the eye, and to acquire, as the measurement data, image data of the OCT scan;
- in a case where one of the plurality of different types of pathology found to be present in the image (400) is a tumour, the method comprises generating (S26), as the respective instruction for the eye measurement apparatus (300) of the selected imaging modality to image the portion of the eye, an instruction for the eye measurement apparatus (300) to perform a high-density optical coherence tomography, OCT, B-scan of the region in the portion of the eye, and to acquire, as the measurement data, image data of the high-density OCT B-scan;
- in a case where the one of the plurality of different types of pathology found to be present in the image (400) is drusen, the method comprises generating (S26), as the respective instruction for the eye measurement apparatus (300) of the selected imaging modality to image the portion of the eye, an instruction for the eye measurement apparatus (300) to perform an optical coherence tomography, OCT, B-scan of the region in the portion of the eye, and to acquire, as the measurement data, image data of the OCT B-scan; and
- in a case where the one of the plurality of different types of pathology found to be present in the image (400) is oedema or atrophy, the method comprises generating (S26), as the respective instruction for the eye measurement apparatus (300) of the selected imaging modality to image the portion of the eye, an instruction for the eye measurement apparatus (300) to perform an optical coherence tomography, OCT, scan of the region in the portion of the eye, and to acquire, as the measurement data, image data of the OCT scan.

E18. The computer-implemented method of E14, wherein, in case at least one of the plurality of different types of pathology is found to be present in the image (400), at least one of the instructions generated is an instruction for an eye measurement apparatus (300) of a selected measurement modality to measure a functional response of the eye to light stimulation.

E19. The computer-implemented method of any of E15 to E17, further comprising generating instructions for controlling a display unit (215) to display the recorded location of the region (410) in the image (400) of the portion of the eye and a representation of the received measurement data.

E20. The computer-implemented method of any of E15 to E17, wherein the learning algorithm (630) is a supervised learning algorithm.

E21. The computer-implemented method of E20, wherein the supervised learning algorithm comprises a neural network, and a region indicative of one of the different types of pathology found to be present in the image (400) is searched for in the image by deconstructing the neural network.

E22. The computer-implemented method of E21, wherein the neural network is a convolutional neural network, and the neural network is deconstructed by:
- performing, for each of a plurality of different sections of the image (400) that is defined by the received image data, processes of:
  - masking (S122) the section of the image (400) to generate a masked image;
  - searching (S124) for the region in the masked image by processing image data defining the masked image using the learning algorithm; and
  - determining (S126) a difference between a result of the search performed using the image data defining the masked image and a result of a search performed using the received image data; and
- determining (S128), as the location to be recorded, a location of a section for which the determined difference is largest.

E23. The computer-implemented method of E21, wherein the neural network is a convolutional neural network, and the convolutional neural network is deconstructed by:
- determining a relevance of each input variable of the neural network to an output of the neural network by applying a Taylor decomposition to each layer of the neural network, from a top layer of the neural network to an input layer of the neural network; and
- determining the location to be recorded based on at least one section of the received image data corresponding to the most relevant input variables of the neural network.

E24. The computer-implemented method of E21, wherein the neural network is a convolutional neural network, and the convolutional neural network is deconstructed by determining a deconvolution of the convolutional neural network.

E25. A computer program which, when executed by a computer, causes the computer to perform a method as set out in at least one of E1 to E24.

E26. A computer-readable storage medium (250) storing the computer program of E25.

E27. A signal (260) carrying the computer program of E25.

E28. An apparatus (100) for searching for a region indicative of a pathology in an image (400) of a portion of an eye acquired by an ocular imaging system (520; 720), the apparatus (100) comprising:
- a receiver module (110) configured to receive image data defining the image (400);
- a search module (120) configured to search for the region in the image (400) by processing the received image data using a learning algorithm (530; 630) trained on image data (502; 604) defining images of the portion of healthy eyes, and image data (601, 602, 603; 501) defining images of the portion of unhealthy eyes each having at least one region that is indicative of the pathology; and
an instruction generating module (130) configured to perform, in response to a region (410) in the image (400) that is indicative of the pathology being found by the search module (120), processes of:
  determining a location of the region (410) in the image (400); and
  generating an instruction for an eye measurement apparatus (300) to perform a measurement on the portion of the eye to generate measurement data, using a reference point based on the determined location for setting a location of the measurement on the portion of the eye,
wherein the receiver module (110) is further configured to receive the measurement data from the eye measurement apparatus (300).

E29. The apparatus (100) of E28, wherein
the search module (120) is configured to search for the region (410) in the image (400) by searching for a region (410) in the image (400) that is indicative of one of a plurality of different types of pathology by processing the received image data using the learning algorithm (630), the learning algorithm (630) being trained on image data (601, 602, 603) defining images of the portion of unhealthy eyes each having a respective one of the different types of pathology,
the instruction generating module (130) is configured to perform, in response to a region (410) in the image (400) that is indicative of one of the plurality of different types of pathology being found by the search module (120), processes of:
  selecting, for the one of the plurality of different types of pathology, a respective one of a plurality of different types of measurement modality for a measurement to be performed on the eye; and
  generating, as the instruction for the eye measurement apparatus (300) to perform the measurement on the portion of the eye, an instruction for an eye measurement apparatus (300) of the selected measurement modality to perform the measurement on the portion of the eye, using the reference point for setting the location of the measurement on the portion of the eye.

E30. The apparatus (100) of E28, wherein
the receiver module (110) is configured to receive, as the image data, image data of a first imaging modality,
the instruction generating module (130) is configured to generate, in response to a region (410) in the image (400) that is indicative of the pathology being found by the search module (120), and as the instruction for the eye measurement apparatus (300) to perform the measurement on the portion of the eye, an instruction for the eye measurement apparatus (300) to perform an image capture process of a second imaging modality to image a region in the portion of the eye, using the reference point for setting, as the location of the measurement, a location of a region in the portion of the eye to be imaged in the image capture process, the second imaging modality being different to the first imaging modality, and
the receiver module (110) is configured to receive from the eye measurement apparatus (300), as the measurement data, image data of the second imaging modality acquired by the eye measurement apparatus (300).

E31. The apparatus (100) of E30, wherein
the search module (120) is configured to search for a region (410) in the image (400) that is indicative of one of a plurality of different types of pathology by processing the received image data using the learning algorithm (630), the learning algorithm being trained on the image data (601, 602, 603) defining images of the portion of unhealthy eyes each having a respective one of the different types of pathology, and
the instruction generating module (130) is configured to perform, in response to a region (410) in the image (400) that is indicative of one of the plurality of different types of pathology being found by the search module (120), a process of selecting, for the one of the plurality of different types of pathology and as the second imaging modality, a respective one of a plurality of different types of imaging modality which is to be used to perform the image capture process on the portion of the eye.

E32. The apparatus (100) of E31, wherein
the instruction generating module (130) is configured to generate, in a case where the one of the plurality of different types of pathology is glaucoma, an instruction for the eye measurement apparatus (300) to perform, as the image capture process of the second imaging modality, an optical coherence tomography, OCT, scan of the region in the portion of the eye, and the receiver module (110) is configured to receive, as the measurement data, image data of the OCT scan;
the instruction generating module (130) is configured to generate, in a case where the one of the plurality of different types of pathology is severe diabetic retinopathy, an instruction for the eye measurement apparatus (300) to perform, as the image capture process of the second imaging modality, an optical coherence tomography, OCT, scan of a region of a retina of the eye, and the receiver module (110) is configured to receive, as the measurement data, image data of the OCT scan;
the instruction generating module (130) is configured to generate, in a case where the one of the plurality of different types of pathology is a tumour, an instruction for the eye measurement apparatus (300) to perform, as the image capture process of the second imaging modality, a high-density optical coherence tomography, OCT, B-scan of the region in the portion of the eye, and the receiver module (110) is configured to receive, as the measurement data, image data of the high-density OCT B-scan;
the instruction generating module (130) is configured to generate, in a case where the one of the plurality of different types of pathology is drusen, an instruction for the eye measurement apparatus (300) to perform, as the image capture process of the second imaging modality, an optical coherence tomography, OCT, B-scan of the region in the portion of the eye, and the receiver module (110) is configured to receive, as the measurement data, image data of the OCT B-scan; and
the instruction generating module (130) is configured to generate, in a case where the one of the plurality of different types of pathology is oedema, an instruction for the eye measurement apparatus (300) to perform, as the image capture process of the second imaging modality, an optical coherence tomography, OCT, scan of the region in the portion of the eye, and the receiver module (110) is configured to receive, as the measurement data, image data of the OCT scan.

E33. The apparatus (100) of E28, wherein, the instruction generating module (130) is configured to generate, in response to the region (410) in the image (400) that is indicative of the pathology being found by the search module (120), and as the instruction for the eye measurement apparatus (300) to perform the measurement on the portion of the eye, an instruction for the eye measurement apparatus (300) to measure a functional response of the eye to light stimulation, using the reference point for setting the location of the measurement which is based on the determined location.

E34. The apparatus (100) of E28, wherein
the receiver module (110) is configured to receive image data representing a result of imaging the portion of the eye using a first value of an imaging parameter, the imaging parameter being one of an imaging resolution, an aperture size and wavelength used in the imaging,
the instruction generating module (130) is configured to perform, in response to a region (410) in the image (400) that is indicative of the pathology being found by the search module (120), a processes of generating, as the instruction for the eye measurement apparatus (300) to perform the measurement on the portion of the eye, an instruction for the eye measurement apparatus (300) to perform an image capture process using a second value of the imaging parameter to image a region in the portion of the eye, using the reference point for setting, as the location of the measurement, a location of a region in the portion of the eye to be imaged in the image capture process, wherein the second value of the imaging parameter is different from the first value of the imaging parameter, and
the receiver module (110) is configured to receive from the eye measurement apparatus (300), as the measurement data, the image data representing the result of imaging the region in the portion of the eye using the second value of the imaging parameter and the received image data and the received measurement data are of the same imaging modality.

E35. The apparatus (100) of any of E28 to E34, wherein the instruction generating module (130) is further configured to generate instructions for controlling a display unit (215) to display the determined location of the region (410) in the image (400) of the portion of the eye and a representation of the received measurement data.

E36. The apparatus (100) of any of E28 to E35, wherein the learning algorithm (630) is a supervised learning algorithm.

E37. The apparatus (100) of E36, wherein the supervised learning algorithm comprises a neural network, and the search module (120) is configured to search for the region indicative of the pathology in the image by deconstructing the neural network.

E38. The apparatus (100) of E37, wherein the neural network is a convolutional neural network, and the search module (120) is configured to deconstruct the neural network by:
performing, for each of a plurality of different sections of the image (400) that is defined by the received image data, processes of:
masking the section of the image (400) to generate a masked image;
searching for the region in the masked image by processing image data defining the masked image using the learning algorithm; and
determining a difference between a result of the search performed using the image data defining the masked image and a result of a search performed using the received image data; and
determining, as the location of the region (410) in the image (400), a location of a section for which the determined difference is largest.

E39. The apparatus (100) of E37, wherein the neural network is a convolutional neural network, and the search module (120) is configured to deconstruct the convolutional neural network by:
determining a relevance of each input variable of the neural network to an output of the neural network by applying a Taylor decomposition to each layer of the neural network, from a top layer of the neural network to an input layer of the neural network; and
determining the location of the region (410) in the image (400) based on at least one section of the received image data corresponding to the most relevant input variables of the neural network.

E40. The apparatus (100) of E37, wherein the neural network is a convolutional neural network, and the search module (120) is configured to deconstruct the convolutional neural network by determining a deconvolution of the convolutional neural network.

E41. An apparatus (800) for searching for the presence of a pathology in an image (400) of a portion of an eye acquired by an ocular imaging system (520), the apparatus (800) comprising:
a receiver module (810) configured to receive image data defining the image (400);
a search module (820) configured to search for the presence of at least one of a plurality of different types of pathology in the image (400) by processing the received image data using a learning algorithm (630) trained on image data defining images (604) of healthy eyes, and images (601, 602, 603) of unhealthy eyes each having a respective one of the different types of pathology; and
an instruction generating module (830) configured to perform, in response to at least one of the plurality of different types of pathology being found to be present in the image (400) by the search module (820), processes of:
selecting, for each of at least one type of pathology found to be present in the image (400), a respective one of a plurality of different types of measurement modality which is to be used to perform a measurement on the portion of the eye; and
generating, for each of the at least one type of pathology found to be present in
the image (400), a respective instruction for an eye measurement apparatus (300) of the respective selected measurement modality to perform the measurement on the portion of the eye,
wherein the receiver module (810) is further configured to receive measurement data of the measurement performed by the eye measurement apparatus (300) of each selected measurement modality.

E42. The apparatus (800) of E41, wherein the search module (820) is further configured to perform, in response to finding at least one of the plurality of different types of pathology to be present in the image (400), a process of:

for each of the at least one of the different types of pathology found to be present in the image (400), searching for a respective region (410) in the image (400) that is indicative of the respective type of pathology, by processing the received image data using the learning algorithm (630), and recording a location of the respective region (410) in the image (400), and the instruction generating module (830) is configured to generate a respective instruction for the eye measurement apparatus (300) of each selected measurement modality to perform a measurement on the eye using a reference point for locating the measurement which is based on the respective location.

E43. The apparatus (800) of E42, wherein the instruction generating module (830) is configured to perform, in response to at least one of the plurality of different types of pathology being found to be present in the image (400) by the search module (820), and for each of the at least one of the different types of pathology found to be present in the image (400), processes of:

selecting a respective one of a plurality of different types of imaging modality which is to be used to image the portion of the eye as the respective one of the plurality of different types of measurement modality; and generating, as the respective instruction for the eye measurement apparatus (300) of the selected measurement modality, a respective instruction for an eye measurement apparatus (300) of the selected imaging modality to image the portion of the eye, using a reference point for locating a region of the eye to be imaged which is based on the respective recorded location, and wherein the receiver module (810) is configured to receive respective image data of the imaging performed by the eye measurement apparatus (300) of the selected imaging modality as the measurement data of the measurement performed by the eye measurement apparatus (300).

E44. The apparatus (800) of E43, wherein:

the instruction generating module (830) is configured to generate, in a case where one of the plurality of different types of pathology found to be present in the image (400) is glaucoma, and as the respective instruction for the eye measurement apparatus (300) of the selected imaging modality to image the portion of the eye, an instruction for the eye measurement apparatus (300) to perform an optical coherence tomography, OCT, scan of the region in the portion of the eye, and the receiver module (810) is configured to receive, as the measurement data, image data of the OCT scan;

the instruction generating module (830) is configured to generate, in a case where one of the plurality of different types of pathology found to be present in the image (400) is severe diabetic retinopathy, and as the respective instruction for the eye measurement apparatus (300) of the selected imaging modality to image the portion of the eye, an instruction for the eye measurement apparatus (300) to perform an optical coherence tomography, OCT, scan of a region of a retina of the eye, and the receiver module (810) is configured to receive, as the measurement data, image data of the OCT scan;

the instruction generating module (830) is configured to generate, in a case where one of the plurality of different types of pathology found to be present in the image (400) is a tumour, and as the respective instruction for the eye measurement apparatus (300) of the selected imaging modality to image the portion of the eye, an instruction for the eye measurement apparatus (300) to perform a high-density optical coherence tomography, OCT, B-scan of the region in the portion of the eye, and the receiver module (810) is configured to receive, as the measurement data, image data of the high-density OCT B-scan;

the instruction generating module (830) is configured to generate, in a case where the one of the plurality of different types of pathology found to be present in the image (400) is drusen, and as the respective instruction for the eye measurement apparatus (300) of the selected imaging modality to image the portion of the eye, an instruction for the eye measurement apparatus (300) to perform an optical coherence tomography, OCT, B-scan of the region in the portion of the eye, and the receiver module (810) is configured to receive, as the measurement data, image data of the OCT B-scan; and the instruction generating module (830) is configured to generate, in a case where the one of the plurality of different types of pathology found to be present in the image (400) is oedema, and as the respective instruction for the eye measurement apparatus (300) of the selected imaging modality to image the portion of the eye, an instruction for the eye measurement apparatus (300) to perform an optical coherence tomography, OCT, scan of the region in the portion of the eye, and the receiver module (810) is configured to receive, as the measurement data, image data of the OCT scan.

E45. The apparatus (800) of E41, wherein the instruction generating module (830) is configured to generate, in response to at least one of the plurality of different types of pathology being found to be present in the image by the search module (820), an instruction for an eye measurement apparatus (300) of a selected measurement modality to measure a functional response of the eye to light stimulation.

E46. The apparatus (800) of any of E42 to E44, wherein the instruction generating module (830) is further configured to generate instructions for controlling a display unit (215) to display the recorded location of the region (410) in the image (400) of the portion of the eye and a representation of the received measurement data.

E47. The apparatus (800) of any of E42 to E44, wherein the learning algorithm (630) is a supervised learning algorithm.

E48. The apparatus (800) of E47, wherein the supervised learning algorithm comprises a neural network, and the search module (820) is configured to search for a region (410) indicative of one of the different types of pathology found to be present in the image (400) by deconstructing the neural network.

E49. The apparatus of E48, wherein the neural network is a convolutional neural network, and the search module (820) is configured to deconstruct the neural network by:

performing, for each of a plurality of different sections of the image (400) that is defined by the received image data, processes of:

masking the section of the image (400) to generate a masked image;

searching for the region in the masked image by processing image data defining the masked image using the learning algorithm; and determining a difference between a result of the search performed using the image data defining the masked image and a result of a search performed using the received image data; and determining, as the location to be recorded, a location of a section for which the determined difference is largest.

E50. The apparatus (800) of E48, wherein the neural network is a convolutional neural network, and the search module (820) is configured to deconstruct the convolutional neural network by:

determining a relevance of each input variable of the neural network to an output of the neural network by applying a Taylor decomposition to each layer of the neural network, from a top layer of the neural network to an input layer of the neural network; and determining the location to be recorded based on at least one section of the received image data corresponding to the most relevant input variables of the neural network.

E51. The apparatus (800) of E48, wherein the neural network is a convolutional neural network, and the search module (820) is configured to deconstruct the convolutional neural network by determining a deconvolution of the convolutional neural network.

E52. An apparatus for searching for a region indicative of a pathology in an image (400) of a portion of an eye acquired by an ocular imaging system (520; 720), the apparatus (100) comprising a processor and a memory storing computer program instructions which, when executed by the processor, cause the processor to perform a method as set out in at least one of E1 to E24.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A computer-implemented method of searching for a region indicative of a pathology in an image of a portion of an eye acquired by an ocular imaging system, the method comprising:
   receiving image data defining the image;
   searching for the region in the image by processing the received image data using a learning algorithm trained on image data defining images of the portion of healthy eyes, and image data defining images of the portion of unhealthy eyes each having at least one region that is indicative of the pathology; and
   in case a region in the image that is indicative of the pathology is found in the searching:
      determining a location of the region in the image;
      generating an instruction for an eye measurement apparatus to perform a measurement on the portion of the eye to generate measurement data, using a reference point based on the determined location for setting a location of the measurement on the portion of the eye; and
      receiving the measurement data from the eye measurement apparatus, wherein
         the received image data represents a result of imaging the portion of the eye using a first value of an imaging parameter, the imaging parameter being one of an imaging resolution, an aperture size and wavelength used in the imaging,
      the eye measurement apparatus is configured to perform, as the measurement on the portion of the eye, an image capture process using a second value of the imaging parameter to image a region in the portion of the eye, and to acquire, as the measurement data, image data representing a result of imaging the region using the second value of the imaging parameter, wherein the second value of the imaging parameter is different from the first value of the imaging parameter, and the received image data and the acquired image data are of the same imaging modality, and
      in the case that a region in the image that is indicative of the pathology is found in the searching, the method comprises:
         generating, as the instruction for the eye measurement apparatus to perform the measurement on the portion of the eye, an instruction for the eye measurement apparatus to perform the image capture process, using the reference point for setting, as the location of the measurement, a location of a region in the portion of the eye to be imaged in the image capture process; and
         receiving from the eye measurement apparatus, as the measurement data, the image data representing the result of imaging the region in the portion of the eye using the second value of the imaging parameter.

2. The computer-implemented method of claim 1, further comprising generating instructions for controlling a display unit to display the location of the region in the image of the portion of the eye and a representation of the received measurement data.

3. The computer-implemented method of claim 1, wherein the learning algorithm is a supervised learning algorithm.

4. The computer-implemented method of claim 3, wherein the supervised learning algorithm comprises a neural network, and the region indicative of the pathology is searched for in the image by deconstructing the neural network.

5. The computer-implemented method of claim 4, wherein the neural network is a convolutional neural network, and the neural network is deconstructed by:
   performing, for each of a plurality of different sections of the image that is defined by the received image data, processes of:
   masking the section of the image to generate a masked image;
   searching for the region in the masked image by processing image data defining the masked image using the learning algorithm; and
   determining a difference between a result of the search performed using the image data defining the masked image and a result of a search performed using the received image data; and
   determining, as the location of the region in the image, a location of a section for which the determined difference is largest.

6. The computer-implemented method of claim 4, wherein the neural network is a convolutional neural network, and the convolutional neural network is deconstructed by:

determining a relevance of each input variable of the neural network to an output of the neural network by applying a Taylor decomposition to each layer of the neural network, from a top layer of the neural network to an input layer of the neural network; and determining the location of the region in the image based on at least one section of the received image data corresponding to the most relevant input variables of the neural network.

7. The computer-implemented method of claim 4, wherein the neural network is a convolutional neural network, and the convolutional neural network is deconstructed by determining a deconvolution of the convolutional neural network.

8. A non-transitory computer-readable storage medium storing a computer program which, when executed by a processor, causes the processor to execute a computer-implemented method according to claim 1.

9. An apparatus for searching for a region indicative of a pathology in an image of a portion of an eye acquired by an ocular imaging system, the apparatus comprising:

a receiver module configured to receive image data defining the image;

a search module configured to search for the region in the image by processing the received image data using a learning algorithm trained on image data defining images of the portion of healthy eyes, and image data defining images of the portion of unhealthy eyes each having at least one region that is indicative of the pathology; and an instruction generating module configured to perform, in response to a region in the image that is indicative of the pathology being found by the search module, processes of:

determining a location of the region in the image; and generating an instruction for an eye measurement apparatus to perform a measurement on the portion of the eye to generate measurement data, using a reference point based on the determined location for setting a location of the measurement on the portion of the eye, wherein the receiver module is further configured to receive the measurement data from the eye measurement apparatus, wherein the receiver module is configured to receive image data representing a result of imaging the portion of the eye using a first value of an imaging parameter, the imaging parameter being one of an imaging resolution, an aperture size and wavelength used in the imaging, the instruction generating module is configured to perform, in response to a region in the image that is indicative of the pathology being found by the search module, a processes of generating, as the instruction for the eye measurement apparatus to perform the measurement on the portion of the eye, an instruction for the eye measurement apparatus to perform an image capture process using a second value of the imaging parameter to image a region in the portion of the eye, using the reference point for setting, as the location of the measurement, a location of a region in the portion of the eye to be imaged in the image capture process, wherein the second value of the imaging parameter is different from the first value of the imaging parameter, and the receiver module is configured to receive from the eye measurement apparatus, as the measurement data, the image data representing the result of imaging the region in the portion of the eye using the second value of the imaging parameter and the received image data and the received measurement data are of the same imaging modality.

10. The apparatus of claim 9, wherein the instruction generating module is further configured to generate instructions for controlling a display unit to display the determined location of the region in the image of the portion of the eye and a representation of the received measurement data.

11. The apparatus of claim 9, wherein the learning algorithm is a supervised learning algorithm.

12. The apparatus of claim 11, wherein the supervised learning algorithm comprises a neural network, and the search module is configured to search for the region indicative of the pathology in the image by deconstructing the neural network.

13. The apparatus of claim 12, wherein the neural network is a convolutional neural network, and the search module is configured to deconstruct the neural network by:

performing, for each of a plurality of different sections of the image that is defined by the received image data, processes of:

masking the section of the image to generate a masked image;

searching for the region in the masked image by processing image data defining the masked image using the learning algorithm; and determining a difference between a result of the search performed using the image data defining the masked image and a result of a search performed using the received image data; and determining, as the location of the region in the image, a location of a section for which the determined difference is largest.

14. The apparatus of claim 12, wherein the neural network is a convolutional neural network, and the search module is configured to deconstruct the convolutional neural network by:

determining a relevance of each input variable of the neural network to an output of the neural network by applying a Taylor decomposition to each layer of the neural network, from a top layer of the neural network to an input layer of the neural network; and determining the location of the region in the image based on at least one section of the received image data corresponding to the most relevant input variables of the neural network.

15. The apparatus of claim 12, wherein the neural network is a convolutional neural network, and the search module is configured to deconstruct the convolutional neural network by determining a deconvolution of the convolutional neural network.

* * * * *